(12) United States Patent
Burnikel

(10) Patent No.: US 9,039,778 B2
(45) Date of Patent: May 26, 2015

(54) MODULAR, ADJUSTABLE, PROSTHETIC, HIP/SHOULDER SPACER

(71) Applicant: Brian G. Burnikel, Greer, SC (US)

(72) Inventor: Brian G. Burnikel, Greer, SC (US)

( * ) Notice: Subject to any disclaimer, the term of this patent is extended or adjusted under 35 U.S.C. 154(b) by 80 days.

(21) Appl. No.: 13/986,254

(22) Filed: Apr. 16, 2013

(65) Prior Publication Data

US 2014/0309745 A1    Oct. 16, 2014

(51) Int. Cl.
*A61F 2/36* (2006.01)
*A61F 2/40* (2006.01)
*A61F 2/30* (2006.01)

(52) U.S. Cl.
CPC .................. *A61F 2/36* (2013.01); *A61F 2/3609* (2013.01); *A61F 2/3662* (2013.01); *A61F 2/40* (2013.01); *A61F 2/4014* (2013.01); *A61F 2/4059* (2013.01); *A61F 2002/30405* (2013.01); *A61F 2002/30492* (2013.01); *A61F 2002/30538* (2013.01); *A61F 2002/30672* (2013.01); *A61F 2002/30677* (2013.01); *A61F 2002/3068* (2013.01); *A61F 2002/3082* (2013.01)

(58) Field of Classification Search
CPC ....... A61F 2/3609; A61F 2/40; A61F 2/4014; A61F 2/4059
USPC .......... 623/18.11, 19.11–19.14, 20.35, 20.36, 623/20.11–20.13, 22.4–22.46, 23.47
See application file for complete search history.

(56) References Cited

U.S. PATENT DOCUMENTS

| | | | |
|---|---|---|---|
| 3,820,167 A | 6/1974 | Sivash et al. | |
| 3,874,003 A | 4/1975 | Moser et al. | |
| 3,996,625 A | 12/1976 | Noiles | |
| 4,261,062 A | 4/1981 | Amstutz et al. | |
| 4,530,114 A * | 7/1985 | Tepic | 623/23.11 |
| 4,550,450 A | 11/1985 | Kinnett | |
| 4,840,630 A | 6/1989 | Kitamura | |
| 5,002,581 A | 3/1991 | Paxson et al. | |
| 5,314,479 A * | 5/1994 | Rockwood et al. | 623/19.14 |
| 5,336,268 A | 8/1994 | Rispeter | |
| 5,358,526 A | 10/1994 | Tornier | |
| 5,645,607 A | 7/1997 | Hickey | |
| 5,681,565 A | 10/1997 | Gristina et al. | |
| 5,702,479 A * | 12/1997 | Schawalder | 623/23.15 |
| 5,728,161 A | 3/1998 | Camino et al. | |
| 5,766,263 A | 6/1998 | Grundi et al. | |
| 6,033,439 A | 3/2000 | Camino et al. | |
| 6,083,263 A | 7/2000 | Draenert et al. | |
| 6,171,341 B1 | 1/2001 | Boileau et al. | |
| 6,238,436 B1 | 5/2001 | Lob et al. | |
| 6,368,352 B1 | 4/2002 | Camino et al. | |
| 6,626,946 B1 | 9/2003 | Walch et al. | |
| 7,238,208 B2 | 7/2007 | Camino et al. | |
| 7,465,319 B2 | 12/2008 | Tornier | |
| 7,678,150 B2 | 3/2010 | Tornier et al. | |
| 2013/0204390 A1* | 8/2013 | Podolsky | 623/22.42 |

* cited by examiner

*Primary Examiner* — Thomas J Sweet
*Assistant Examiner* — Brian Dukert
(74) *Attorney, Agent, or Firm* — Stephen R. Chapman

(57) ABSTRACT

A modular, adjustable, prosthetic hip/shoulder spacer adapted to being implanted in the hip or shoulder joint; the spacer comprises a frame that supports a rotatable cylinder from which a neck extends with the ball element of the joint attached to its end, and rotating the cylinder reposition the ball in the socket; the stem is connected to the base of the frame and is implanted in the long bone (femur or humerus); the stem may be modified to include a system for delivering medication to the implantation site following surgery. The stem leg and stem base may be modified to form a modular unit to adjust the relation between a center line of the stem leg and a center line of the frame and position of the neck and ball.

4 Claims, 23 Drawing Sheets

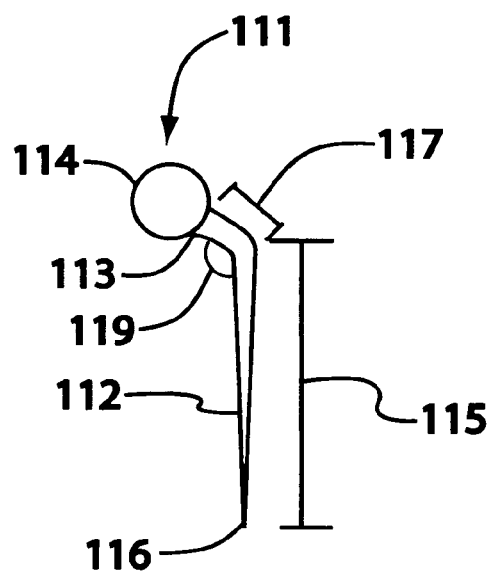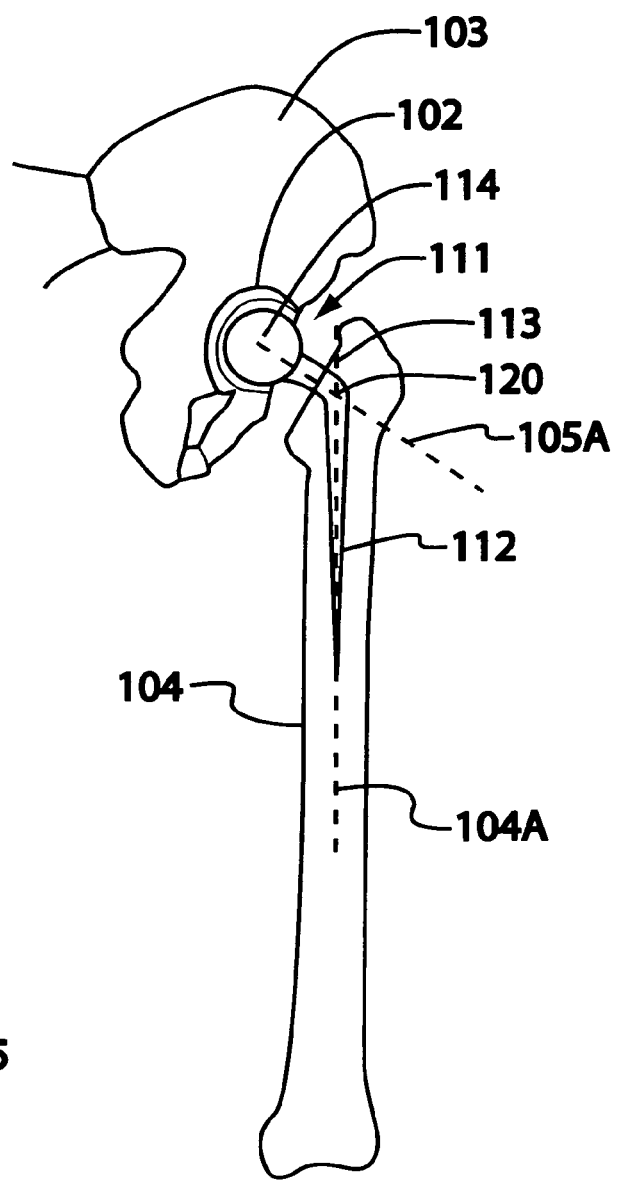
FIGURE 1C
FIGURE 1D

MODULAR, ADJUSTABLE, PROSTHETIC, HIP/SHOULDER SPACER

FIELD OF THE INVENTION

The invention is directed generally to the field of prosthetic devices. It is more specifically directed to implantable devices, and it is specifically directed to an implantable prosthetic device to be used following the removal of a prosthetic joint device when a temporary implant is required to stabilize a joint or as part of infection treatment.

GENERAL BACKGROUND

Introduction

The medical profession and general public recognize the benefits of the continued development of prosthetic implant technology-including advances in surgical techniques and technology and pre- and post-operative patient care and rehabilitation. Orthopaedic implant devices remain on the cutting edge of this complex field.

Artificial hip and knee joints comprise the majority annual surgical implant procedures performed in the United States, over 300,000 hip joint replacements annually, and approaching 400,000 knee replacement surgeries annually. Shoulder replacement surgery is rapidly increasing, approaching 25,000 replacements annually, Hip Replacement Hip replacement surgery is reportedly the most successful and reliable orthopaedic implant surgery performed; ninety percent or more of the patients report positive results from the surgery.

From 80 to 90% of the hip surgeries require no replacement (revision) surgery. A variety of factors contributes to the need for subsequent, prosthetic replacement procedures: normal wear and tear on the artificial joint (particularly as the age of patients is decreasing and activity levels are increasing), accidents and injuries to the original implant; bone degeneration and degenerative diseases; and joint infections (regardless of the site of the initial infection). Treatment of an infection may require removal of the original artificial joint involving more than one surgical procedure prior to implanting a new prosthesis.

Basic Hip Anatomy

Understanding the basic skeletal anatomy of the hip joint provides the necessary foundation for understanding the structure and function of hip prosthetic devices. The hip joint is a "ball and socket" joint. The hip joint involves the head of the femur and the hip socket (acetabulum cup) which is part of the hip bone. In practice, implanting the prosthetic device involves the femur (thigh bone) per se.

Hip replacement surgery may be performed as a total joint replacement procedure, or as a partial replacement procedure depending on conditions to be remedied by replacement.

The femoral head or ball of the hip joint is replaced in both total and partial replacement procedures. The basic surgical procedures are common in either case. Thus the discussion of femoral head replacement (ball replacement) applies to both procedures. Total replacement involves consideration of restructuring/resurfacing the socket and such are not directly relevant to the current invention that involves only the replacement of the femoral head, even if the procedure is a complete replacement.

FIG. 1A provides a simplified anterior view of the left hip joint 101 showing the relationship only of the major skeletal parts. The hip joint 101 comprises the socket (or cup) 102 formed as a part of the hip bone 103 and the ball or femoral head 105 formed at the proximal end of the femur 104. For reference purposes, the knee joint 108 is indicted at the distal end of the femur 104.

For reference purposes, the vertical center line of the femur 104A and center line of the ball 105A are shown. The same reference lines (104A and 105A) are shown in FIG. 1D to suggest orientation of parts of the femoral prosthesis 111 in relation to the natural hip joint. The center line of the ball 105A intercepts the center line of the femur 104A at a point above the proximal end 104B of the femur 104. As one skilled in the art understands, the precise orientation of the ball/femur center lines may vary among individuals; matching natural orientation is an important consideration in surgery.

FIG. 1A also indicates a common condition leading to a partial hip replacement surgery. A fracture 107 has partially (or completely) separated the femoral head (ball) 105 from the femur 104. The fracture 107 is indicated in the neck region 106 of the femur, between the ball 105 and the greater trochanter 109; the lesser trochanter 110 is indicated for reference.

FIG. 1B illustrates in exaggerated dimension the space 106A left by amputating the damaged portion of the femoral head (ball) 105 and segment of the neck region 106 including the fracture 107 in the neck region 106, critical steps in surgical preparation for a partial (or complete) hip joint replacement surgery.

Hip Joint Replacement

Basic Femoral Implant

FIG. 1C illustrates the basic elements of a femoral hip implant 111 used in partial hip replacement procedures, and FIG. 1D illustrates the femoral hip implant 111 as it might be positioned during a partial hip replacement procedure. Note FIG. 1D is comparable to FIG. 1A: front views of the left hip. The femoral hip implant 111 comprises three distinct, but contiguous segments: the stem 112, the neck 113, and the ball 114. The stem 112 with its distal tip 116 is inserted into the femur 104; the neck 113 is contiguous with the stem 112, and the post engages the female receptacle of the ball 114 thereby connecting the ball to the stem. The prothesis may be manufactured with the ball 114 as an integral part of the joint or the ball 114 may be manufactured separately and a female receptacle of the ball 114 engages the male post and securely connects the ball 114 with the neck 113.

Part of the preparation of the femur is amputation of injured or diseased bone material to insure sound bone material to anchor/support the stem. The ball 114 is connected to the neck region 113. Conceptually and practically, the neck region 113 replaces the bony tissue removed in preparing the femur to receive and anchor the femoral hip implant 111. The length of the neck 117 establishes the offset defined as the distance from the axis or centerline of the stem 104A to the centerline of the ball 105A. The offset distance reflects natural variation among individuals as a result of size and shape of the hip bone(s) and femur. The angle 119 between the centerline of the stem 104A and a centerline 105A of the ball as it extends to the femur (extending the length of the neck 206) varies with the length of the stem 115, offset, and position of the ball 114 in the socket 102 all of which factors are mutually dependent. Length of the stem 115 is depends in part on the extent of bone removal in preparing the femur for the stem implant, which, in conjunction with natural variation in bone size and shape offset.

Dimensions of the femoral hip implant 111 vary obviously with respect to the size and bone structure of the recipient. The stem 112 varies in length 115 from 175 to 200 mm and may be slightly tapered longitudinally with an average, maximum diameter of approximately 9 mm. Commonly, the distal tip of the stem 116 comes to a somewhat rounded or blunted point.

The femoral hip implant 111 (FIG. 1C) is inserted into the femur 104 such that the stem 112 is positioned in relation to the center line 104A of the femur and the ball 114 is positioned in the socket 102. The stem 112 and ball 114 are connected by the neck 113. The angle 119 of the neck and stem are functions of the length of the stem and of offset.

Revision Surgery

Revision surgery is the removal and replacement of an artificial joint. For hips, it may involve both the socket and femoral component, or only the femoral component. Conditions leading to revision hip surgery include wear and tear on the original implant, post implant injury to the pelvis, hip, or thigh, and infections around the implant. In some instances, the infection cannot be treated effectively without removal of the implant.

Prior Art

Hip Replacement

The present application focuses on, but is not limited to devices designed to replace a hip endoprosthetic device for various reasons, one of which may be infection, the treatment of which is a primary concern of the replacement surgery. Implanting a temporary replacement prosthetic device may be a significant consideration related to optimum treatment of infections and final outcome of the final replacement surgery.

Prior Art: Endoprosthetic Hip Joints

In the past 40 years various aspects of artificial hip joint technology have been the subject a number of US and foreign patents. The following references primarily reflect the field of technology disclosed and claimed in the instant application, the femoral portion of an endoprosthetic hip joint use in partial hip replacement procedures.

Initial US patents considered total hip replacements—hip socket and femoral stem with neck. The femoral stem and neck are relevant to both complete and partial hip replacement surgeries.

For example U.S. Pat. No. 3,820,167 issued Jun. 28, 1974 to Sivash, et al. claims an acetabular prosthesis of the cotyloid cavity defining a socket and having blades to engage the walls of the cotyloid cavity, and the prosthesis head of the femur in addition to a pin and neck, and also includes an enlarged shoulder/femoral collar for positioning the femoral pin in the femur. U.S. Pat. No. 3,874,003 issued Apr. 1, 1975 to Morse and Karpf describes a stem and ball unit and socket, as well as a collar to minimize twisting the stem. Similarly, U.S. Pat. No. 3,918,102 issued Nov. 11, 1975 to Eichler includes both the femoral component (ball and stem) and socket. U.S. Pat. No. 3,996,625 issued Dec. 14, 1976 to Noiles discloses and claims a device comprising an acetabulum prosthesis defining a socket and a femoral prosthesis including a pin (stem) to be driven into the bone marrow channel of the femur.

The use of specific materials for hip prosthetic devices has not received extensive consideration, at least in US patents. U.S. Pat. No. 4,840,630 issued Jun. 20, 1987 to Kitamura represents an exception. The section of the prosthetic device directly contacting the hip bone is made of a ceramic material, and a socket plug that supports the condyle of a stem member is made of plastic. The patent recognizes strength of the ceramic material as a practical limitation.

Increasing emphasis has been placed on hip joint prosthetic devices in which the angle of the stem to the neck and/or ball, positioning of the ball in the hip socket, and rotation of the ball (or neck) in relation to the stem receive significant, if not primary emphasis. U.S. Pat. No. 5,002,581 issued Mar. 26, 1991 to Paxon and Stamp discloses and claims a modular hip prosthesis with provisions for varying the angulation between the stem trochanteral modular portions by connection between the neck and stem which can be positioned or connected in a variety of rotational positions.

U.S. Pat. No. 5,336,268, issued to Aug. 9, 1994 to Rispeter claims an adjustable hip joint endoprosthesis capable of absorbing overloads which otherwise could result in damage to the prosthesis part implanted in the femur (the stem) and require reimplantation. An adjustable prosthesis head is connected with the stem that is fixed in the femur. A limiting element in the prosthesis head absorbs the overload by deformation (sliding), thereby avoiding serious damage or injury; however, after the overload, the limiting element (not the entire prosthesis) must be replaced or reset. Draenert and Piper in U.S. Pat. No. 6,083,263 issued Jul. 4, 2000 disclose and claim an endoprosthetic hip joint with a head virtually identical to the head described in FIG. 1 of U.S. Pat. No. 5,336,268 compared with FIG. 1 and FIG. 2 of U.S. Pat. No. 6,083,263.

Additional variations in endoprosthetic hip joints have been described in US patents. For example, Lob, et al., in U.S. Pat. No. 6,238,436 issued May 29, 2001, claim a modular artificial hip joint comprising a head part and at least one shaft part. The shaft part can be driven into the bone (femur) and forms the distal region and is connected to the distal end of the head part by insertion. A screw or comparable device traverses an axial bore in the head and engages a threaded bore in the shaft part. A second screw separates the conical insert connection between the components of the artificial joint. Grundi and Scholz, U.S. Pat. No. 5,766,263 issued Jun. 16, 1998 disclose and claim a femur endoprosthetic device comprising a shell which can be implanted in the femur without the use of a cement material. The proximal end of the shell can be connected by an adapter to an artificial, spherical joint. The joint is partially covered by an open-meshed, three-dimensional lattice structure and draw plate.

U.S. Pat. No. 5,645,607 issued Jul. 8, 1997 to Hickey discloses and claims a provisional (very temporary) prosthetic device designed to assist the surgeon in determining the optimum lengths and angles of a permanent hip prosthesis. The offset is adjustable over a series of fixed points and the neck is secured to the base by a pivot rod held by a spring against the base. The function of the pivot rod and spring allows the pivot rod to be moved such that the neck can be moved and repositioned with respect to the base, thereby allowing the physician to determine optimum lengths and angles of the neck for the permanent implantment.

Treatment and control of infections has become part of the emerging technology of endoprosthetic hip joints. U.S. Pat. No. 5,681,565, issued to Gristina and Giridhar on Oct. 28, 1997 presents a detailed discussion of experimental results for methods and materials used in conjunction with endoprosthetic devices for applications of immunoglobulins to tissues surrounding Wounds and biomaterial implants, including endoprosthetic devices and claims methods for delivery of immunoglobulins to such sites.

Basic Shoulder Anatomy

The shoulder joint, like the hip joint, is a ball and socket joint. The complete anatomy of the shoulder joint may be more complex than that of the hip; this is clearly suggested by the more extensive range of motion of the shoulder compared with the hip. These obvious differences not withstanding, the skeletal anatomy of the shoulder, FIG. 2A is comparable to the anatomy of the hip, FIG. 1A.

The shoulder joint 220 connects the arm to the rest of the body. The shoulder joint 220 comprises two major elements: the humerus or upper arm bone 221, comprising the long bone segment 222 and the head 223. The humerus head 213 comprises the ball 223A and the neck element 223B. For convenience and illustrative purposes the humerus 221 (specifically, the ball 223A) may be considered the male element of the shoulder joint.

The shoulder joint 220 further comprises the scapular element 224, which by analogy with the humerus 221, may be considered the female element of the shoulder joint (socket 235). The female, scapular element 224 comprises the scapula 225 (commonly recognized as the shoulder blade) and the collar bone 226. The collar bone 226 comprises the clavicle 227 and the acromion 228. The acromion 228 is a process formed along the top of the spine of the scapula 225 and is joined to the clavicle to form the collar bone 226. The coracoid process 229 comprises a bony growth that functions as an anchor point for a variety of shoulder and arm muscles. Finally, the glenoid fusa 230, or socket element, is formed at the upper, outer edge of the scapula 225. The socket 235 engages the ball 223A to connect the humerus 222 to the body, through the scapula element 224, supported in part by the collar bone 226, with the associated muscles, ligaments, and tendons (not illustrated).

Shoulder joint replacement surgery may be the result of a variety of conditions or factors, fractures (line 231) of the ball 223A or similar injuries, arthritis, infections, and damage to a previously implanted prosthetic device. Shoulder joint replacement surgery involves amputation of the ball 223A and a portion of the neck 223B (the humerus head 223) as illustrated in FIG. 2A and FIG. 2B. For illustrative purposes, FIG. 2A indicates a fracture indicated by line 231. As one skilled in the art understands, index number 231 could also indicate a variety of conditions for which surgery resulting in the amputation of a part of the humerus head 223 would be amputated. Line 232 indicates the line of the amputation. FIG. 2B illustrates the results of the amputation along line 232 (FIG. 2A) and the space 234 left open as the result of the amputation of a portion of the humerus head 223. Other parts are identified for reference purposes, following FIG. 2A.

FIG. 2C illustrates the shoulder joint 220 in FIG. 2A and FIG. 2B with an implanted shoulder joint prosthesis. One skilled in the art recognizes the marked similarities between the hip joint illustrations of FIG. 1A and FIG. 1D and the shoulder joints of FIGS. 2A and 2C. Also, one skilled in the art recognizes that the same type of prosthetic devices may be adapted for both hip and shoulder joint prosthetic replacements.

The shoulder joint in FIG. 2C is the same as the joint illustrated in both in FIG. 2A and FIG. 2B in which the socket 230 is formed as part of the scapula (shoulder blade) 225 with the supporting collar bone 226. The joint prosthesis 233 is positioned with the ball 233A in the socket and physically connected to neck 233B, and the stem 233C is positioned in the humerus 222. The positioning of the neck 233B is shown in relation to the amputation line 232

Prior Art: Endoprosthetic Shoulder Joint

Surgery to replace shoulder joints is far less common than hip joint replacement surgery. Technological advances developed for one of these joints frequently benefits the other joint. Although the joints may appear to be very different, their mutual ball and socket skeletal anatomy establishes a fundamental similarity; this similarity is reflected in similarities is joint prosthetic devices and is apparent in a variety of US patents. The common anatomical base in its simplest sense is seen in the fact that replacement joints (prosthetic devices) for both the shoulder and hip commonly have at least a stem, a neck, and a ball. The same endoprosthetic device may be used in either hip or shoulder replacement surgery.

U.S. Pat. No. 7,465,319 issued Dec. 16, 2008 to Tornier describes and claims an endoprosthetic device that can be adapted for hip or shoulder replacement purposes, including a process for fitting the device. The basic elements common to both hip and shoulder joint prosthesis include the stem adapted to being positioned in the femur (hip replacement) or humerus (shoulder replacement) and in the concave surface of the articulation femoral or humeral component formed by a plate connected by the neck to a part (stem) adapted to be secured in the medullary cavity of the femur or humerus.

Numerous shoulder prosthetic devises are similar to hip devices but are designed or modified specifically for the shoulder. Kinnett in U.S. Pat. No. 4,550,450, issued Nov. 5, 1985 describes and claims a device adapted specifically for replacement of the articular surfaces of the humerus and the adjacent glenoid articular surfaces. Rather than a stem to connect the device to the humerus, the device includes a trapezoidal fixation keel that connects the device to the humerus and avoids violation of the medullary cavity. The device further comprises a concave over-mounted glenoidal cavity with a similar keel.

U.S. Pat. No. 4,261,062 and issued Apr. 14, 1981 to Amstutz and Clarke discloses a complete shoulder joint prosthesis. The prosthetic joint comprises humeral element comprising a metal ball and stem secured at the upper end of the humerus, and a glenoidal element and a concave, plastic prosthesis with a keel having a cross-section shape of the corresponding glenoidal recess (shoulder socket). The metal stem has a longitudinal rib to prevent rotation of the stem when implanted in the humerus. The plastic glenoidal element is elliptical at the articulating surface and within the glenoidal recess to conform with the natural shape of the joint.

U.S. Pat. No. 7,678,150 issued Mar. 16, 2010 to Tornier, Walch, and Boileau in which the cup element of the shoulder prothesis is positioned on the humerus and the corresponding ball element is positioned on the glenoidal element of the shoulder. The glenoidal component comprises a convex articulating surface positioned in near the glenoidal cavity and the humeral component comprises a concave element adapted to functionally engage the glenoidal convex element.

Comino, Snyder, and Urbahns in U.S. Pat. No. 6,368,352 issued Apr. 9, 2002 describes and claims a kit for the assembly of a modular joint prosthesis. The prosthesis, in kit form, comprises shank body elements adapted to be inserted into the shank of the bone and head members sized to replace one bearing member of the joint. One end of the shank is formed into a collar, adapted to engage and secure the head member's open cavity. Each kit provides more than one head member and shank to allow assembling of various combinations of the head and shank sizes and angles with respect to the shoulder socket.

U.S. Pat. No. 6,626,946 issued Sep. 30, 2003 to Walch and Boileau discloses and claims a prosthesis comprising a stem and a hemispherical cap adapted to engage the shoulder socket. The stem fits into the humeral canal. The stem further comprises an upper or metaphyseal part including a bearing surface against which the hemispherical cap rests. The stem is selected from an array of stems, each having a different tilt angle with respect to the longitudinal axis of the individual stem.

U.S. Pat. No. 7,238,208 issued Jul. 3, 2007 to Comio, et al. discloses and claims a joint prosthesis the parts of which comprise parts included in the kit for assembling a modular joint prosthesis of U.S. Pat. No. 6,638,352. See also, U.S. Pat. No. 6,033,439 issued Mar. 7, 2000 to Comino, Snyder and Urbahns and U.S. Pat. No. 5,728,161 issued Mar. 17, 1998 to Comino, Snyder, and Urbahns.

U.S. Pat. No. 5,358,526 issued Oct. 25, 1994 to Tornier describes a modular humeral prosthesis comprising three main elements. First, a humeral stem adapted to anchor the device in the humerus. The stem includes a bearing face. Second, a wedge shaped spacer with a first face adapted to fit on the bearing face of the stem. Third, a humeral cap with a flat base which is fixed with respect to the second face of the spacer. The attachment of the cap and spacer relative to the bearing face of the stem allows the cap to be adjusted angularly around an axis off-set from the axis of symmetry of the cap. The cap engages the shoulder socket; the cap is locked to the spacer, and the spacer is locked to the stem.

U.S. Pat. No. 6,171,341 issued to Boileau and Walch on Jan. 9, 2001 discloses a shoulder joint prosthesis that comprises a rod that is inserted into and anchored in the humerus; a metaseal element of the rod extends upward and inward from the humerus. The metaseal element is attached at a connection point to a flange that supports a hemispherical cap that is adapted to engage the shoulder socket. The connection is position so as to establish a clear zone for joining and fusing osseous fragments of the metaphysis.

Adjustable, Prosthetic Hip/Shoulder Spacer

Goals and Objectives

A first goal and objective of the invention is a prosthetic device that is adaptable to be implanted for the hip or shoulder joint.

A second goal and objective of the invention is a neck positioning cylinder that allows the position/orientation of the neck and ball in relation to the joint cup to be adjusted during surgery.

A third goal and objective of the invention is a stem adapted as part of the medication delivery system that includes a refillable medication reservoir A fourth goal and objective of the invention are interlocking, modular elements that allow the positioning/orientation of the stem in the long bone and the orientation of the interlocked modular segments to be adjusted during surgery.

A fifth goal and objective of the invention is simplicity in adjusting one or more parts, components, or elements of the invention during surgery without disturbing all other parts or requiring removal of the entire prosthetic device.

A sixth goal or objective of the invention is a series of stem legs varying in length by a common increment and in diameter and each stem leg being adapted to engaging and being secured by the threaded female receptacle of the stem base.

These and other goals and objectives can be achieved by a modular, adjustable, prosthetic, hip/shoulder spacer that comprises a frame, a neck positioning cylinder (NPC), a neck, and a stem, and in which the frame comprises a cradle that supports the neck positioning cylinder with an axle that secures the cylinder in the cradle and either locking pins or complimentary grooves on the cylinder surface and corresponding cradle floor interlock and prevent the cylinder from rotating around the axle and the locking pins serve the same function; the neck is connected to the cylinder with a ball at the opposite end of the neck that engages and connects the neck to the hip or shoulder joint socket; rotating the cylinder allows the ball to be optimally positioned in the socket and then locked in that position; the stem descends from the bottom of the frame and is inserted into the long bone of the hip (the femur) or the shoulder (the humerus) to connect the long bone, through the frame and neck with the ball connecting the neck to the socket; in certain circumstances the stem is made in two pieces, the base that is part of the frame and the elongated stem leg; stem legs are made in different lengths and diameters that all fit the stem base and that may be needed for special conditions; also, in some circumstances, the capacity to deliver medication along the stem to the long bone is desirable; the stem may be coated with medication for this purpose, and the surface of the stem may be texturized to increase the amount of medicine that can be delivered; in addition, the stem may be modified to include an medication delivery system including a supply reservoir and chamber for medication that is part of the stem base and stem leg; finally the top of the stem and the bottom of the frame may be modified into interlocking adjustable modular segments that allow the relationship of the frame and stem to be adjusted with respect to positioning of the stem in the long bone; the modular units may be separated, removed, and repositioned during surgery to ensure the best surgical results.

BRIEF DESCRIPTION OF THE FIGURES

FIG. 1C illustrates a simple device used in hip joint replacement.
FIG. 1D illustrates the device of FIG. 1C implanted in the femur with the ball positioned in the socket.

THE BASIC DEVICE

Figure 3A:
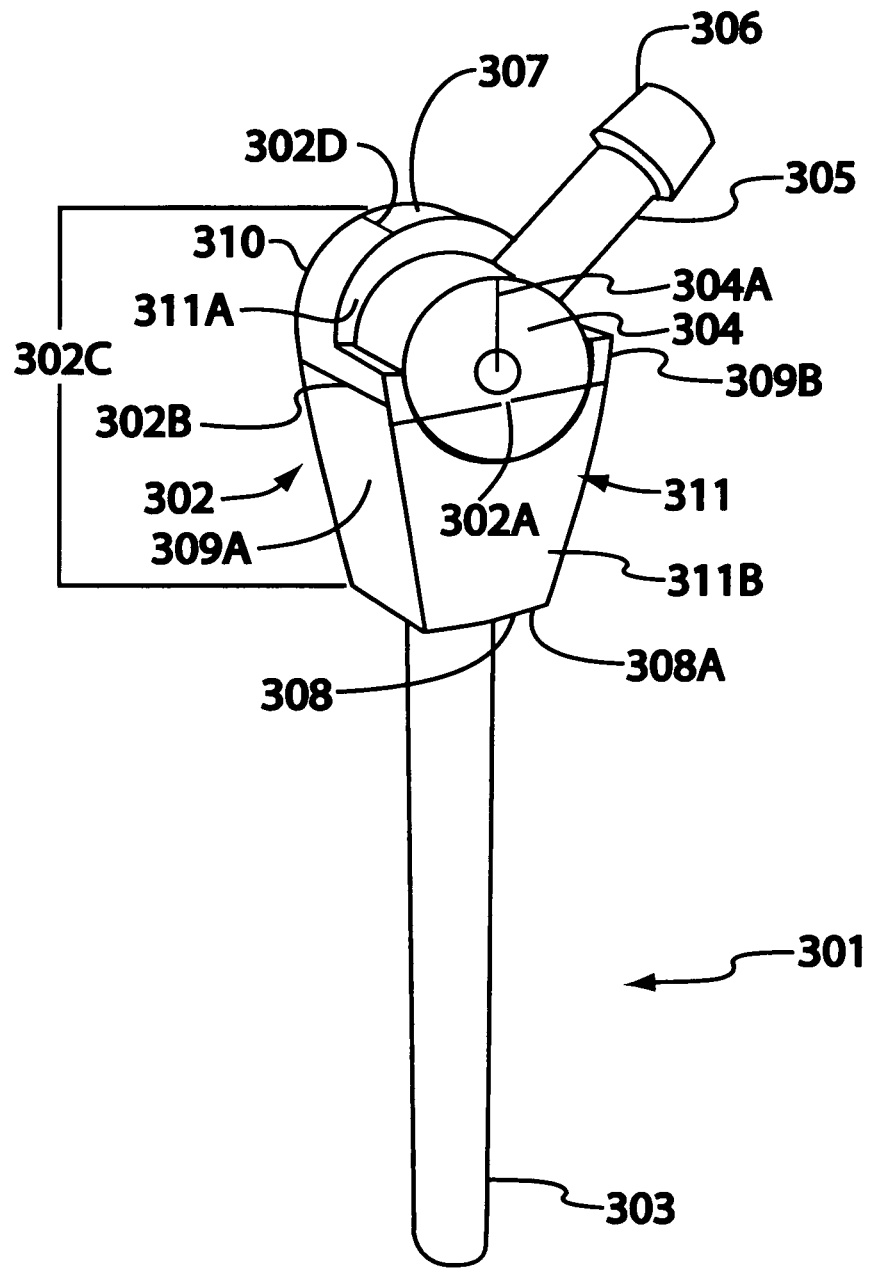
FIG. 3A provides an overview of the modular, temporary, prosthetic hip/shoulder spacer.

As illustrated in FIG. 3A, the modular, adjustable, prosthetic, hip/shoulder spacer (MAPH/SS) 301 comprises five interconnected basic, modular elements: the frame 302, the stem 303, the neck positioning cylinder (NPC) 304 with a solid core, the neck 305, and the ball 306. Dimensions of the five parts may vary as a function of the application of the MAPH/SS as a hip spacer versus the application as a shoulder spacer.

Figure 3B:
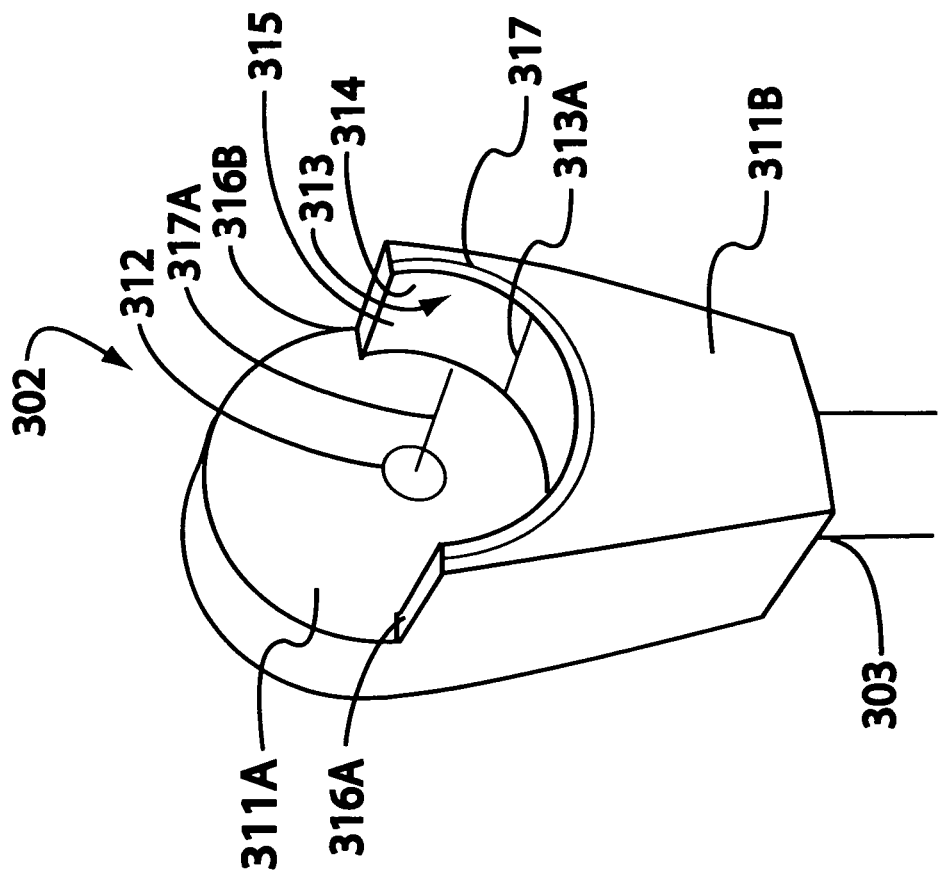
FIG. 3B illustrates the general structure of the frame of the device in FIG. 3A.

The frame 302, FIGS. 3A and 3B, is manufactured from, preferably, a single solid metal or metallic alloy block, such as titanium or other material well known to those skilled in the art. The frame 302 comprises a top 307, a bottom surface 308, a bottom line 308A, first and second ends 309A and 309B, respectively, that are contiguous with the top 307 and the bottom 308 (along bottom line 308A), and a first face 310 and a second face 311. The second face 311 comprises an upper second face 311A and a lower second face 311B. The top 307 is contiguous with the first face 310 and with the second upper face 311A and has a width 302D and is defined by a top line 307A and a length 307B. The width of the top 307 may vary as a function of the shape of the first and second ends 309A and 309B, respectively. The first 309A and second 309B ends may extend in an upward arc to join at a common line, thereby effectively eliminating a defined top without altering or extending the scope or intent of the invention; such extensions and modifications are anticipated by and included in the scope and intent of the invention. The frame 302 is further defined by a width 302A, a height 302C, and a thickness or depth 302B.

In application, but not limitation, the frame 302 may reasonable but not exclusively be described by the following approximate dimensions. Width 302A varies from 19.1 to 50.8 mm (0.75 to 2.00 in); overall depth or thickness 302B varies from 25.4 to 50.8 mm (1 to 2 in); and overall height 302C varies from 44.5 to 57.1 mm (1.75 to 2.25 in). Width 302D of the top 307 varies from 12.7 to 18.0 mm (0.50 to 0.75 in).

The lower half of the second face 311B comprises the NPC 313. The NPC 313 functionally includes a semi-circular cradle bed 314, with a solid bed floor 315 and parallel first 316A and second 316B ledges defining the upper limits of the NPC 313. The arc 317 defining the semi-circular geometry of the NPC 313 is specifically defined by the radius 317A of the circle with center point 312 on the surface of the upper half second face 311A. The length of the arc 317B is generally less than one-half of the circumference of the circle defined by radius 317A. The radius 317A is equal in length to the radius 304A of the NPC 304, which, by way of example, not limitation, varies from 12.7 to 38.1 mm (0.5 to 1.5 in); and the depth 313A of the NPC 313 equals the length (or width) 330 of the NPC 304 (FIG. 3D).

Figure 3C:
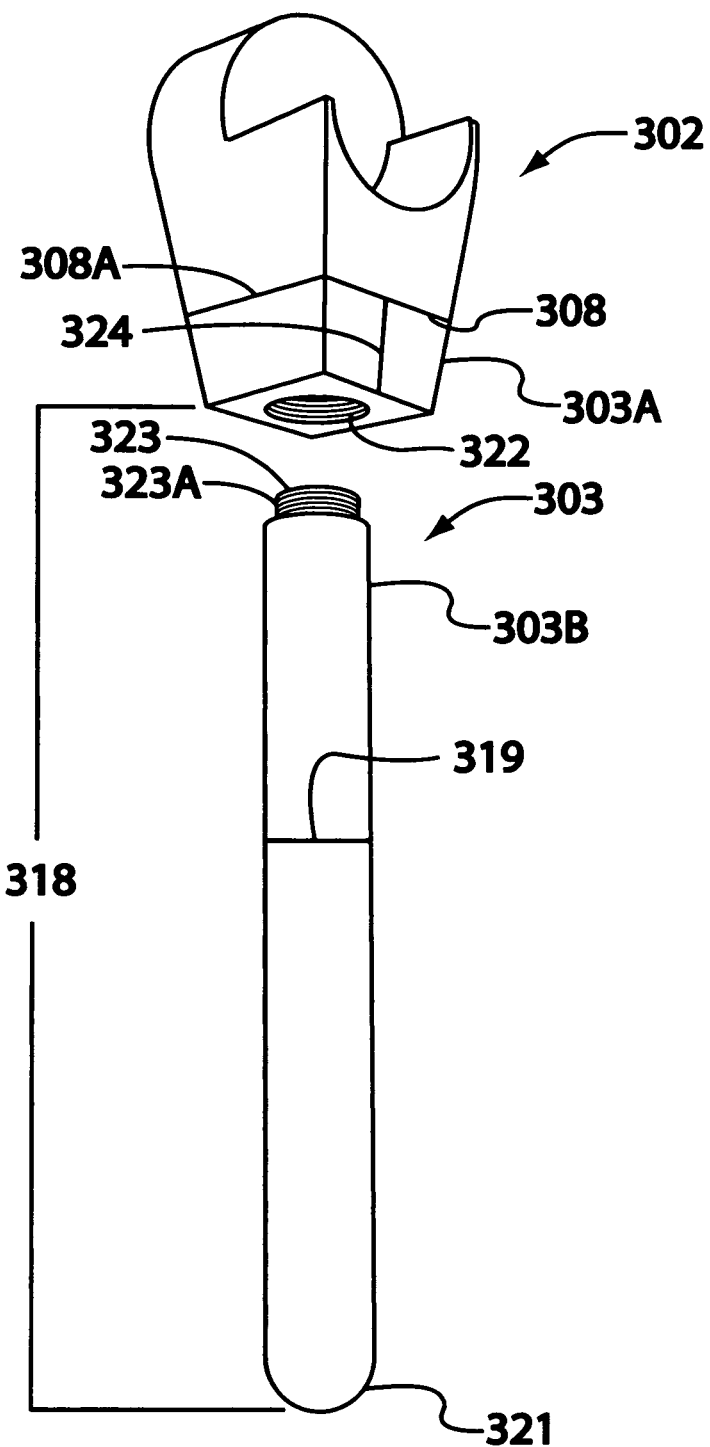
FIG. 3C illustrates an alternative stem structure.
Figure 3D:
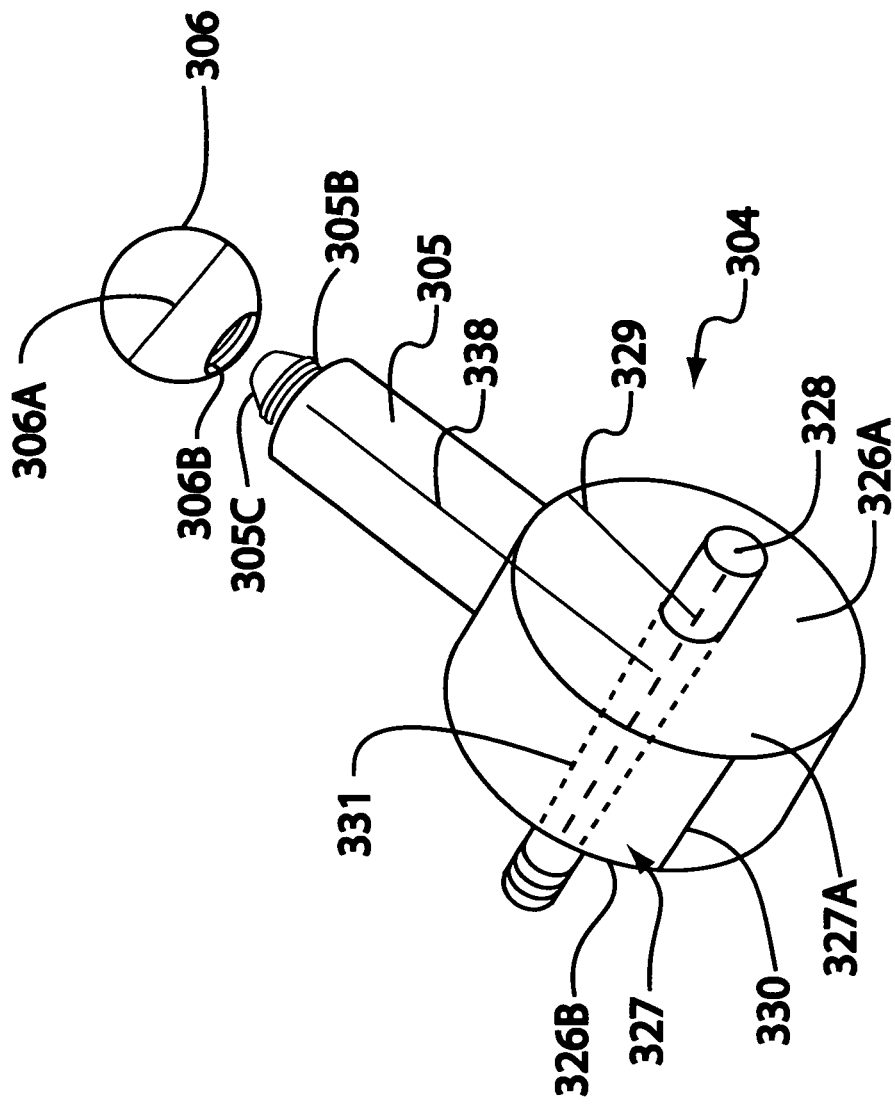
FIG. 3D shows neck arm securely connected to NPC with ball separated from neck.

FIG. 3C illustrates the structure of the stem and the structural relationship between the stem and the frame 302. The stem 303 comprises two separate units—the stem base 303A and the stem leg 303B. The stem base 303A is contiguous with and structurally a part of the bottom 308 of the frame 302. The upper limit of the stem base is the bottom line 308A, for identification and descriptive purposes. The stem base 303A comprises a threaded, female receptacle 322, and the proximal end 323 of the stem leg 303B a male, threaded connector section 323A adapted to engage and functionally to connect the stem base 303A and stem leg 303B. The length 324 of the stem base 303A varies, by way of example, not as a limitation, from about 12.7 to about 19.1 mm (0.50 to 0.75 in), and the length 318 of the stem leg 303B ranges for example from about 160.0 to 220.0 mm (about 6.33 to 8.66 in). Specific length is a medical decision made by the surgeon on an individual case basis, and at times made during surgery in response to unanticipated conditions, as one familiar with the art understands. Stem legs vary in increments of 5 mm with common dimension of the male connector section 323A adapted to a common, female receptacle 322. The stem leg 303B is the portion that is positioned in and engages the femur to connect the frame 302 to the leg (thigh) as previously described.

The NPC 304 is a structure with a solid core 327A comprising the first 326A and second 326B circular end faces and the circumference surface face 327 and a center point 328 that extends as a center line 325A longitudinally through the core 327A. The NPC 304 has a radius 329 that equals the radius 317A from the center point to the bed floor 315 of the semi-circular cradle bed 314, which, by way of example, not limitation, varies from about 25.4 to about 50.8 mm (1.00 to 2.00 in). The width 330 of the NPC 304 equals the length 313A of the semi-circular cradle bed 314.

Figure 3E:
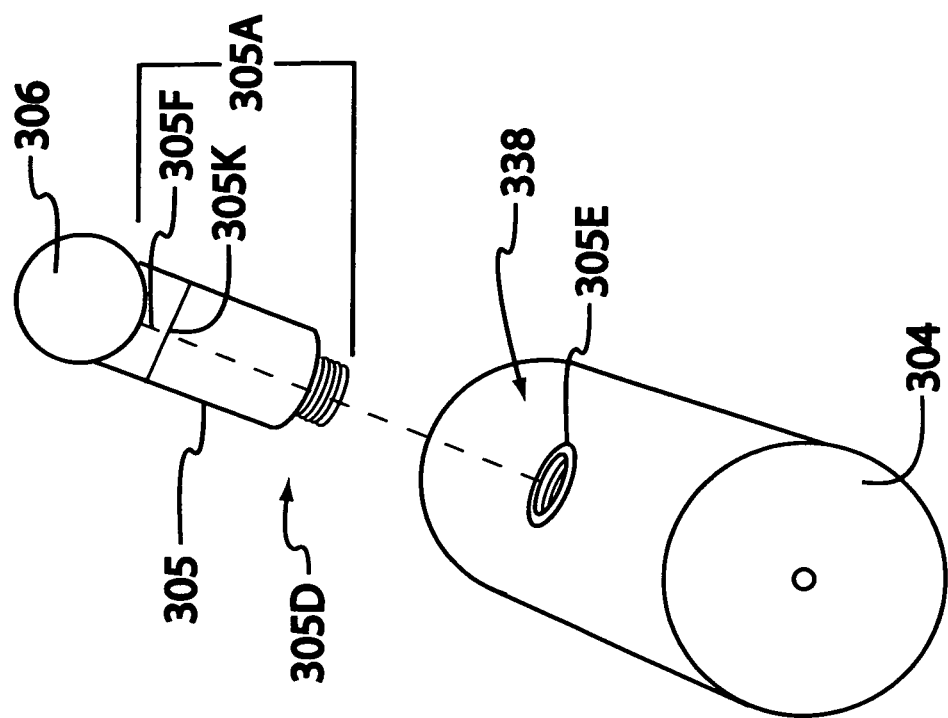
FIG. 3E shows ball securely connected to the neck arm with neck arm separated from NPC.

FIG. 3E shows the neck 305 mechanically engaged with and positioned on the NPC 304. The neck 305 extends on a radius line 338 from the center line of the NPC 304. FIG. 3D shows the ball 306 engaged with the distal end 305B of the neck 305 and the NPC 304 and the and the threaded proximal end 305D aligned 333 with the threaded receptacle 305E on the NPC 304.

By way of example, not limitation, the length 305A of the neck 305 varies from about 40.00 to about 60.00 mm (1.57 to 2.36 in), and the diameter 305K by way of example varies from approximately 6.35 to 8.39 mm (0.25 to 0.33 in).

The distal end 305B is threaded and shaped in a post configuration 305C. The ball 306 varies in diameter 306A with a common diameter of commercially available balls being 28 mm (1.12 in). The ball 306 comprises a female receptacle 306B with a shape and dimensions complimentary to the shape and dimensions of the post 305C such that the post 305C may functionally engage the female receptacle 306B thereby securing the ball 306 to the neck 305. The ball 306 engages and connects the hip socket to the neck 305.

The neck arm 305F comprises a length 305G and a diameter 305K. The diameter 305K varies, by way of example, not limitation, from about 4 to about 6 mm (0.16 to 0.25 in). The length 305G varies in increments of 6 mm (0.025 in) such that the overall length 305A may vary from about 40 to 60 mm (1.57 to 2.36 in). The length of the neck base 305D varies from about 12.7 to about 19.1 mm (0.50 to 0.75 in). Such variation in the length of the neck arm 305F accommodates increased/decreased overall length 305A which affects positioning of the ball 306 in the hip socket 102.

Figure 3F:
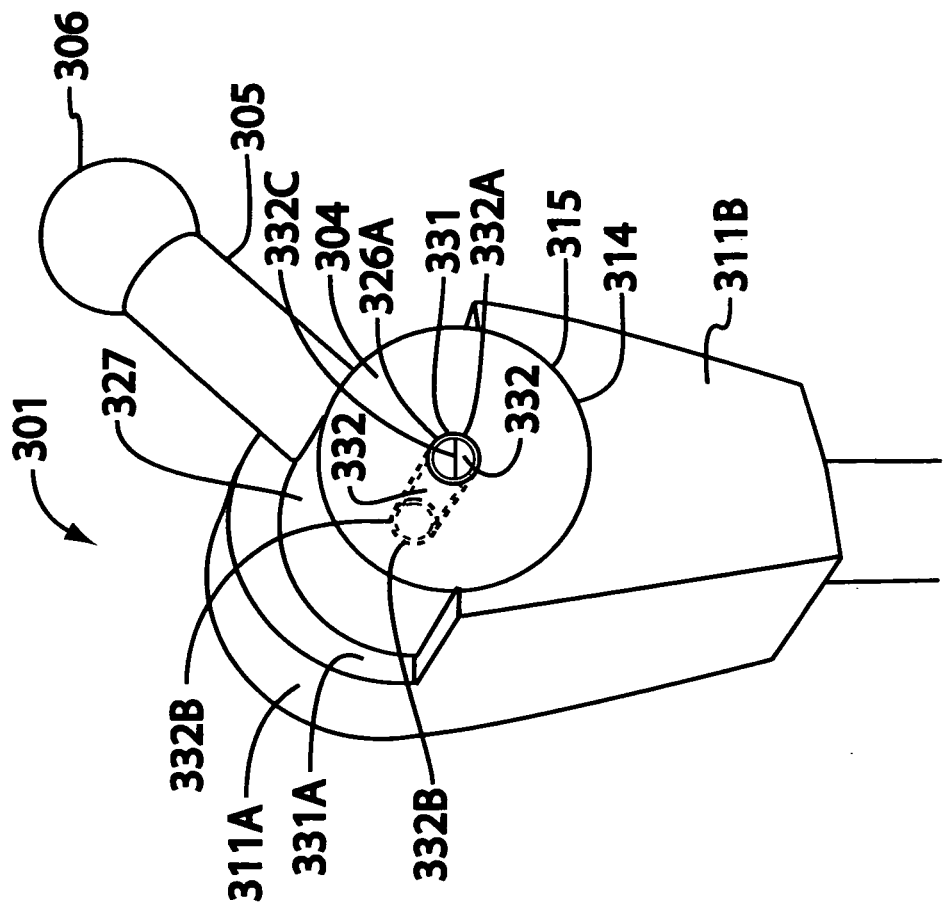
FIG. 3F illustrates NPC positioned in the cylinder cradle.
Figure 3G:
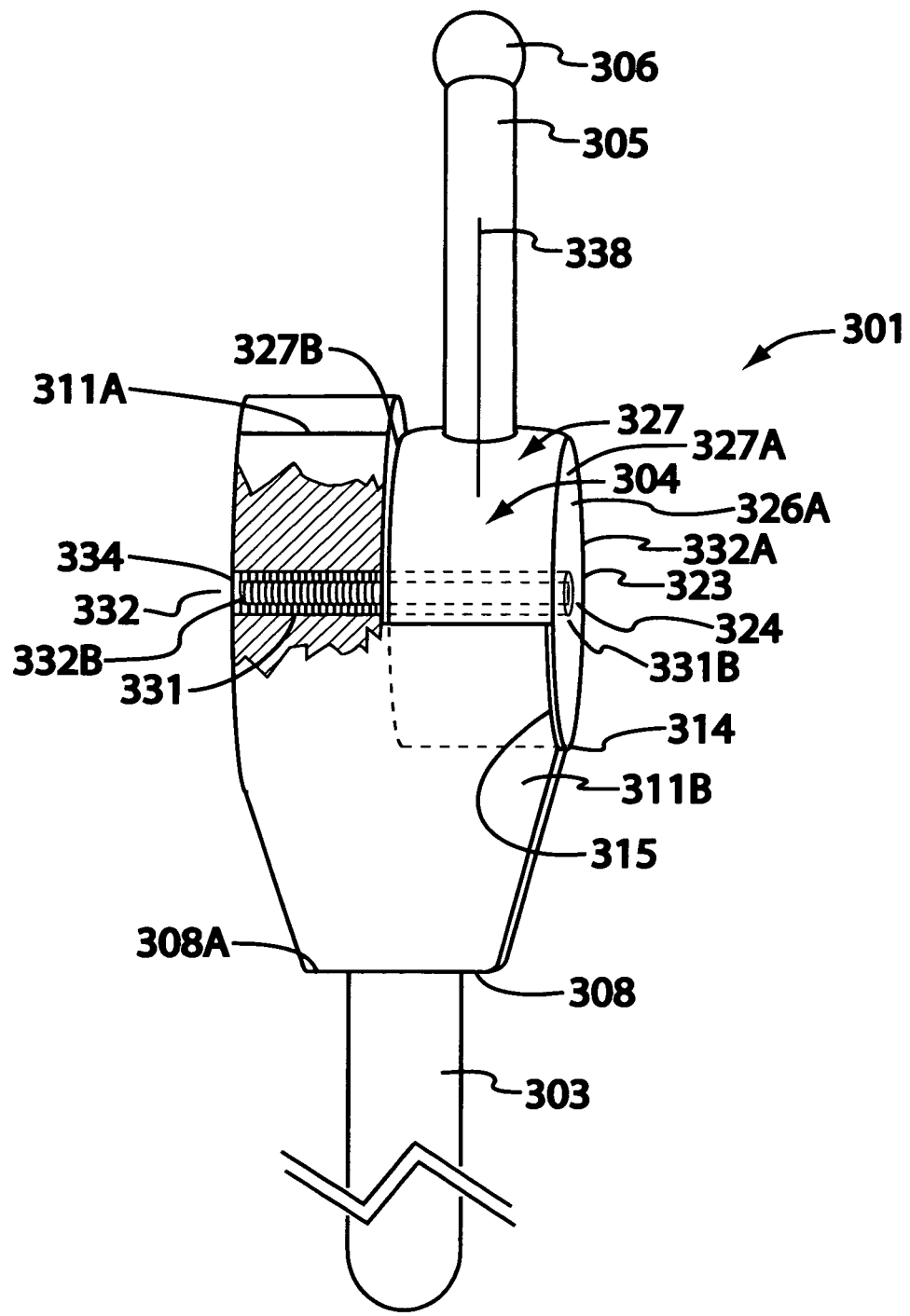
FIG. 3G shows end view of fully assembled device of FIG. 3A.

FIGS. 3F and 3G illustrate the complete modular, adjustable, prosthetic, hip/shoulder spacer (MAPH/SS) 301. Note, FIG. 3A also illustrates the complete modular, adjustable, prosthetic hip/shoulder spacer 301 with details of the frame, but lacking details of the semi-circular cradle bed 314 in place.

The NPC 304 is positioned in the semi-circular cradle bed 314 such that the circumference surface 327 is in contact with the solid bed floor 315. The axle 332 traverses the axle chase 331, and the threaded, distal end 332B of the axle 332 engages the threaded female anchor receptacle at the center point 233 of the upper half second face 311A. (See FIG. 3G for cross-section detail). The proximal end 332A of the axle 332 comprises a slotted head that is tightened against a recess in the first face 326A of the NPC.

FIG. 3G illustrates the NPC 304 positioned in the semi-circular cradle bed 314 with the circumference face/surface 327 resting on the solid floor 315. The axle chase 331 traverses the neck positioning wheel 304 and extends through the second face upper half 311A becoming the threaded axle anchor receptacle 331A. The axle 332 extends through the axle chase 331 and the threaded, distal end 332B of the axle 332 engages the threaded axle anchor receptacle 331A and secures the NPC 304 in the semi-circular cradle bed 314. The proximal end 332A of the axle 332 comprises a head that is secured in a recessed cup 328 in the proximal end 331B of the axle chase 331. The ball 306, neck 305, second face lower half 311B, the bottom 308, bottom line 308A, stem 303 and frame 302 are identified for reference purposes and to facilitate comparisons among related figures.

Figure 4A:
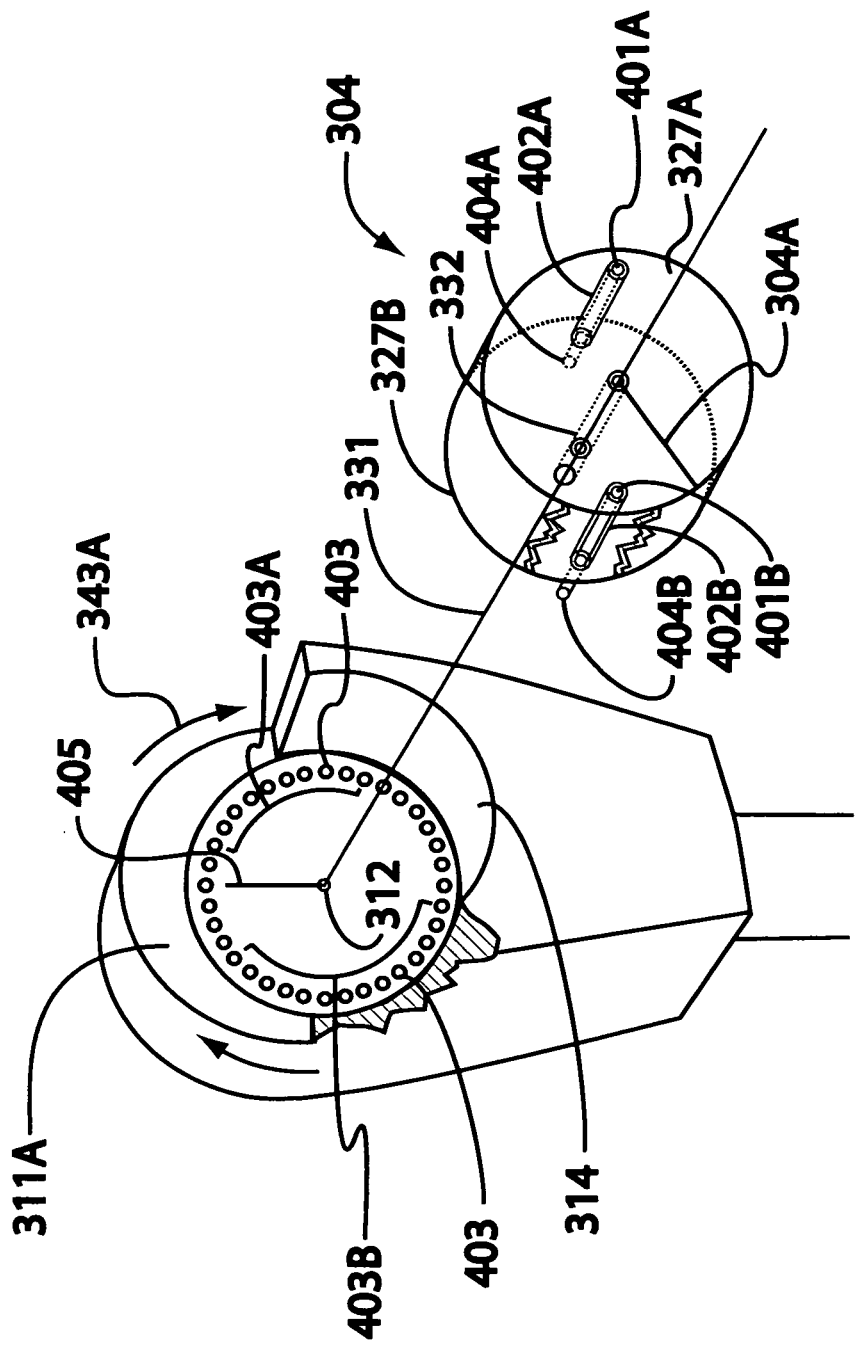
FIG. 4A illustrates details of pin locking to prevent neck NPC from rotating around axle.
Figure 4B:
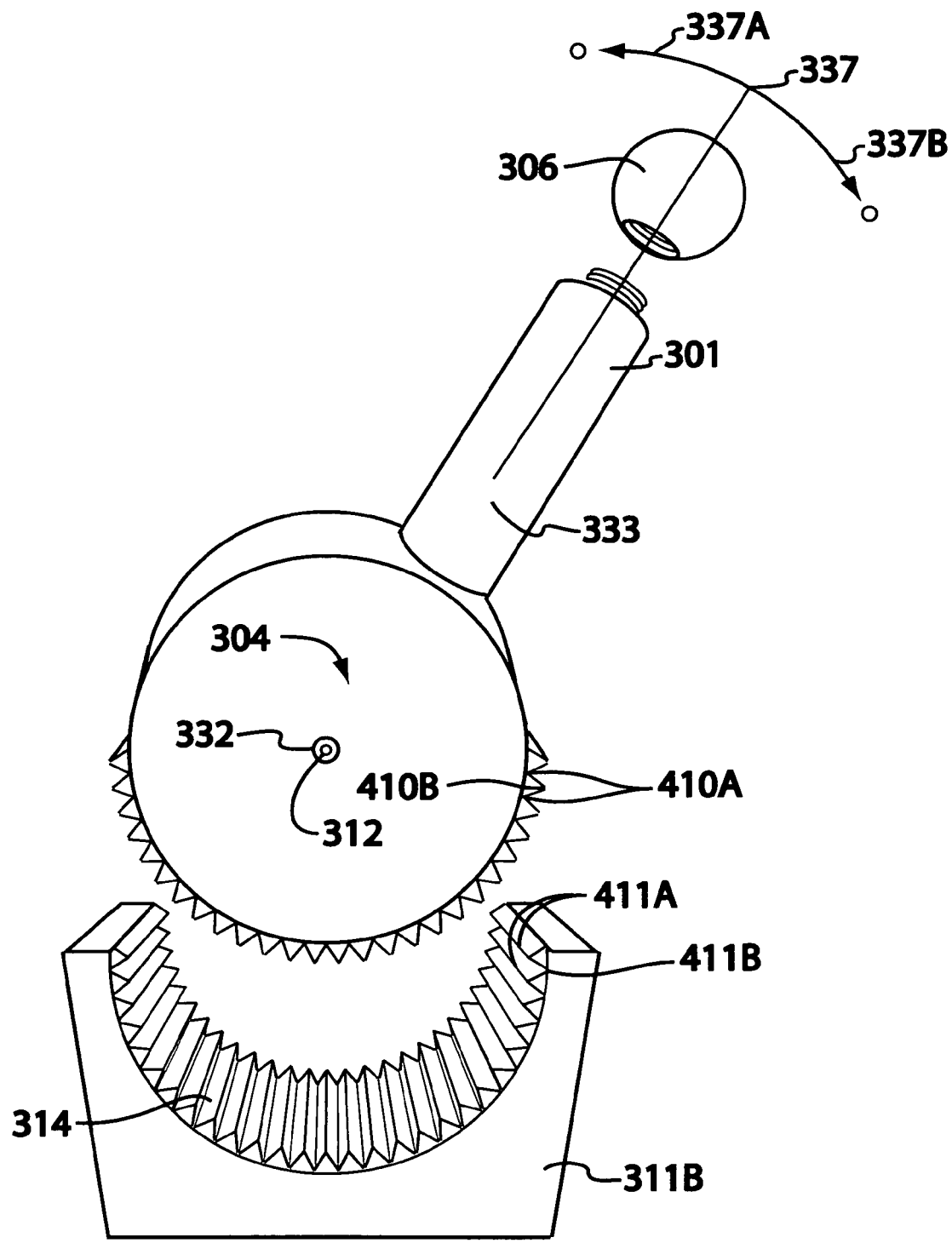
FIG. 4B illustrates alternative locking mechanism to prevent the NPC from rotating around axle.

The NPC 304 may be rotated during surgery to reposition the ball 306 in an optimal position/orientation. Once the position is established, the neck positioning cylinder must be locked in that position. FIG. 4A illustrates locking the NPC 304 to prevent rotation around the axle 332 when the cylinder surface face 327 is positioned directly on the solid bed floor 315 of the semi-circular cradle bed 314. Details of the axle 332 and axle chase 331 are shown in FIG. 3G.

The NPC 304 slides onto the cradle bed 314, and the cylinder surface face 327 is in direct contact with the solid bed floor 315. The axle 332 traverses the longitudinal dimension of the NPC 304 via the axle chase 331, and the distal end 332B of the axle 332 engages the threaded anchor receptacle 334, thereby securing the neck positioning cylinder 304 in the cradle bed 314. The NPC 304 rotates on the axle 332 to position the ball 306 in the in the joint (hip or shoulder) socket. When properly positioned during surgery, the NPC 304 is locked in position by one of three alternative cylinder position locking devices, two utilizing locking pins and one engaging complimentary grooves and ridges on the modified cylinder surface face 327 and modified solid bed floor 315 of the cradle bed 314.

As illustrated in FIG. 4A, each member of a pair of locking pins 401A and 401B traverses the NPC 304 through a corresponding locking pin chase 402A and 402B. Each locking pin chase, 402A and 402B, traverses the NPC 304 from its first, outer face 327A through its second inner face 327B. One member of the pair of locking pins 401A or 401B is secured in a corresponding locking pin receptacle arranged in two corresponding groups 403A and 403B. The distal end 404A or 404B of the corresponding locking pin 401A or 401B engages a corresponding receptacle from the first 403A or second 403B groups of locking pin receptacles. The locking pin receptacles are bored into the second upper face 311A at a distance 405 from the center point 312, and the receptacles in each group are positioned along an arc such that adjacent members of first group 403A are separated by a distance equal to 20 degrees along the arc, and members of the second group 403B are similarly spaced. Alternating receptacles between the first and second group 403A and 403B allows spacing of 10 degrees. Inserting either the first 401A or second 401B locking pin prevents the NPC 304 from rotating on the axle 332.

The spacing of the locking pin receptacles and locking the NPC 304 allows controlled rotation of the NPC in 10 degree increments considering the following. The first set 403A and second set 403B of locking pin receptacles are positioned on an arc with a radius 406 extending from the center point 312/center line 331 to a first and to a second locking pin chase 402A and 402B respectively. The length of the radius 406 equals the distance 405 extending from the center point 312/center line 331 to the first and second locking pin chase 402A, and 402B, respectively. This distance is less than the radius 304A of the NPC 304. The first set of locking pin receptacles 403A comprises by way of illustration six individual receptacles, with adjacent receptacles spaced in even, 20 degree increments on the arc defined by radius 406, and the second set of receptacles 403B comprises six individual receptacles spaced in odd, 20 degree increments on the arc defined by radius 406.

Positioning the NPC 304 is initially accomplished by sliding the neck positioning cylinder 304 onto the cradle bed 314 and loosely securing the neck positioning cylinder with the axle 332 and aligning the first locking pin 401A with a receptacle of the first set of locking pin receptacles 403A. If the neck 305 and ball 306 are not positioned properly, the axle 332 is loosened, but not removed, and the previously positioned locking pin 403A is removed. The neck/ball are re-positioned by rotating the NPC 304 manually. Adjustment increments are achieved by aligning either the first locking pin 401A with a receptacle from the first set (20 degree increments) or by removing the first locking pin 401A and positioning the second locking pin 401B in the first nearest receptacle of the second set of locking pin receptacle 403B yielding an initial 10 degree adjustment; there after adjustments will be by odd, 20 degree increments, unless the first locking pin is employed, in which case returning to (or alternating between) the sets of locking pin receptacles (403A and 403B) will result in continuous 10 degree adjustments.

The NPC 304 can be rotated around the axle 332 approximately 50 degrees above 337A or 50 degrees below 337B an arbitrary horizontal reference point 337. With the ball properly positioned in the socket, the axle 332 traverses the NPC 304 via the axle chase 331. As the distal end 332B of the axle 332 is secured in the threaded anchor receptacle 324, complimentary grooves and ridges formed parallel to each other and to the axle chase on the cylinder face surface 327 and solid floor 315 of the cradle bed 314 engage to prevent the NPC 304 from rotating around the axle 332. Adjacent wheel grooves 410A are machined and form and define a parallel wheel ridge 410B. On the opposing, semi-circular cradle bed 314, pairs of parallel ridges 411 machined on the solid bed floor 315. Each pair of bed ridges 411A defines and limits a bed groove 411B. With the ball 306 properly positioned in the socket, the neck positioning cylinder 304 is positioned in the semi-circular cradle 314 such that the wheel ridges 410B engage the complimentary bed grooves 411B, and the bed ridges 411A engage the complimentary wheel ridges 410B thereby securing the neck positioning cylinder 304 and preventing rotation of the NPC 304 and movement of the ball 306 in the socket.

Figure 4C:
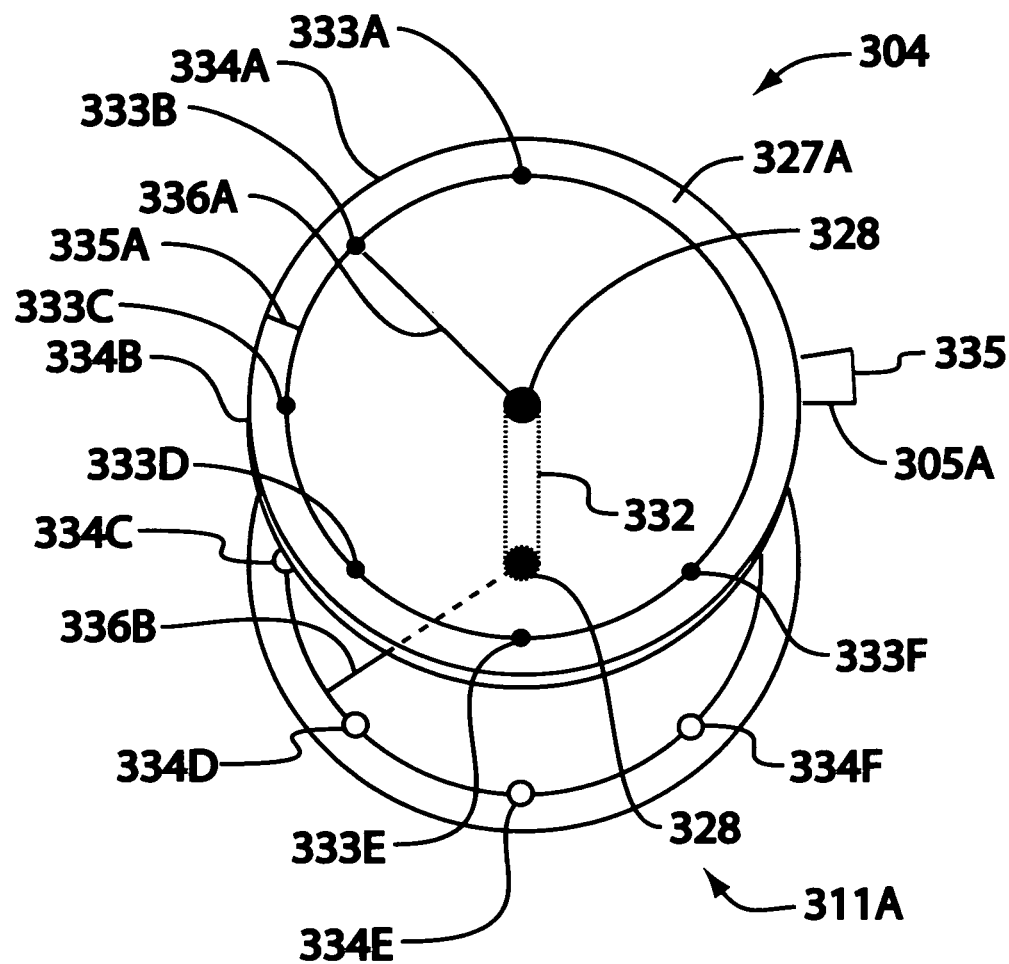
FIG. 4C illustrates another pin locking arrangement to prevent the NPC from rotating around the axle.

A third locking means as illustrated in FIG. 4C, recognizes, but does not specifically limit the range (or arc) in which the arm 305 (or ball 306) may be adjusted or the increments of adjustments. In practice, the range of adjustment, taken from the horizontal, varies from 5 to 90 degrees upward, preferably from 10 to 50 degrees in increments of from 10 to 15 degrees.

FIG. 4C by way of illustration, not limitation, shows adjustments over a range of 60 degrees in 10 degree increments.

The NPC 304 is positioned in the cradle 314 and secured by an axle 332, as previously described with respect to FIGS. 3A,G, and H. The locking means comprises two sets of locking pin chases with each set having six members. The members of the first set designated 333A,B,C,D,E, and F are bored through the NPC 304 from the face 327A through the back face 327B, and the members of the second set designated 334A,B,C,D,E, and F are bored through the second upper half 311A as previously described with respect to FIG. 4A.

The six members of the first set of locking pin chases 333A,B,C,D,E, and F are positioned on an arc 335A the center point of which is the same as the center point of the axle 332. The radius 336A of the arc 335A is less than the radius 329 of the NPC 304. (See FIG. 3D).

The six members of the second set of locking pin chases are positioned on the upper second half 311A on an arc 335 with the same center point 332 and radius 336B as the center point 332 and radius 336A as the first set of locking pin chases 333A,B,C,D,E, and F.

With the neck 305 positioned horizontally, the members of the first set of locking pin chases are positioned as follows, in order: the first member 333A is at the base position at a right angle to the arm; the second member 333B is positioned 45 degrees counter clockwise from the first member 333A; the third member 333C is positioned 45 degrees counter clockwise from the second member 333B (and 90 degrees counter clockwise from the first member 333A); the fourth member 333D is positioned 45 degrees counter clockwise from the third member 333C (90 degrees from the second member 333B, and 135 degrees counter clockwise from the first member 333A); the fifth member 333E is positioned 45 degrees counter clockwise from the fourth member 333D (90 degrees from the third member 333C, 135 degrees from the second member 333B, and 180 degrees counter clockwise from the first member; and, the sixth member 333F is positioned 45 degrees clockwise from the fifth member (90 degrees from the fourth member 333D, 135 degrees from the third member, 180 degrees from the second member, and 225 degrees counter clockwise from the first member). Each of the members of the first set of locking pin chases is 45 degrees counter clockwise from the preceding member such that, except for chases 333A and 333F, there is 45 degrees between adjacent locking pin chases.

The six members of the second set of locking pin chases or threaded receptacles are arrayed in a similar pattern on the upper second half 311A as follows: with the first member 334A of the second set of locking pin chases positioned directly in line with the first member 333A of the first set of locking pin chases, the second member 334B of the second set of locking pin chases or threaded receptacles is positioned counter clockwise 55 degrees from the first member 334A; the third member 334C of the second set is positioned counter clockwise 55 degrees from the second member 334B of the second set; the fourth member 334D is positioned 55 degrees counter clockwise from them third member 334C, the fifth member 334E is positioned 55 degrees counter clockwise from the fourth member 334D, and the sixth member is positioned 55 degrees counter clockwise from the fifth member. The resulting pattern of the members of the second set of locking pin chases or receptacles is the same as the pattern for members of the first set; spacings are different. Adjacent members are separated by 55 degrees in the second set, such that moving counter clockwise from the first member 334A, the second member 334B is 55 degrees from the first member 334A; the third member is 110 334C degrees from the first member 334A, the fourth member 334D is 155 degrees from the first member 334A; the fifth member 334E is 215 degrees from the first member, and the sixth member 334F 270 degrees from the first member 334A.

Members of the first set of locking pin chases are bored through the NPC 304 on the arc 335A and the rotate with the cylinder with respect to members of the second set of locking pin chases bored in the upper second half 311A. One and only one member of the first set of locking pin chases is aligned with a corresponding member of the second set. For example, with the first members 333A and 334A of the first and second sets of locking pin chases aligned, the second member of the first set 333B is 10 degrees clockwise (clockwise) the second member of the second set 334B, and the third member of the first set 333C is 20 degrees behind the third member second set, and so forth for the fourth, fifth, and sixth members of each set. Rotating the neck positioning cylinder 10 degrees 335 counter clockwise from its initial position aligns the second member of the first set 333B with the second member of the second set 334B such that the locking pin can engage the aligned chases.

The same rotation moves the third member of the first set 333C to a position 10 degrees behind the third member of the second set, and a subsequent adjustment of 10 degrees would align the third members of both sets, and so forth for the fourth, fifth, and sixth members of each set. As one skilled in the art recognizes, the initial 45 degree separation of the members of the first set and 55 degrees of members of the second set provides the 10 degree spacing for rotation between points. However, rotation will only allow alignment of one pair of chases.

The six members of the first set locking, pin chases 333A-F are smoothly bored and the members of the second set 334A-F are threaded along the distal ¾ of their length such that with slight pressure on the locking pin positioned in any member of the first set of locking pin chases 333A-F, the pin will "snap" into (initially engage) only one appropriately aligned member of the second set of chases 334A-F and be secured to lock the NPC and prevent its further rotation, thereby locking the arm and ball in position.

One skilled in the art recognizes that the spacings of 45 and 55 degrees is arbitrary, the interval spacing is established by this difference which could have been 65 and 75 degrees (or 20 and 30 degrees) for example. In addition, one skilled in the art recognizes that in addition to the locking pins described, other means to lock the neck positioning cylinder could be employed, such as, but not limited to keys, rather than pins. In this case, slots, not chases would be positioned on the cylinder and in the second upper half 311A. The invention anticipates various other locking means and spacings in addition to those specifically described above.

Infection Treatment and Control

Stem Leg Coatings

In addition to connecting the frame 302 of the MAPH/SS 301 to the femur, the stem 303, or specifically that portion of the stem implanted in the femur (e.g. the stem leg 303A or its equivalent), the stem 303 provides a physical structure by which antibiotic materials can be delivered to points/areas in the femur following surgery, depending on the formulation and dosage of medication.

Figure 5A:
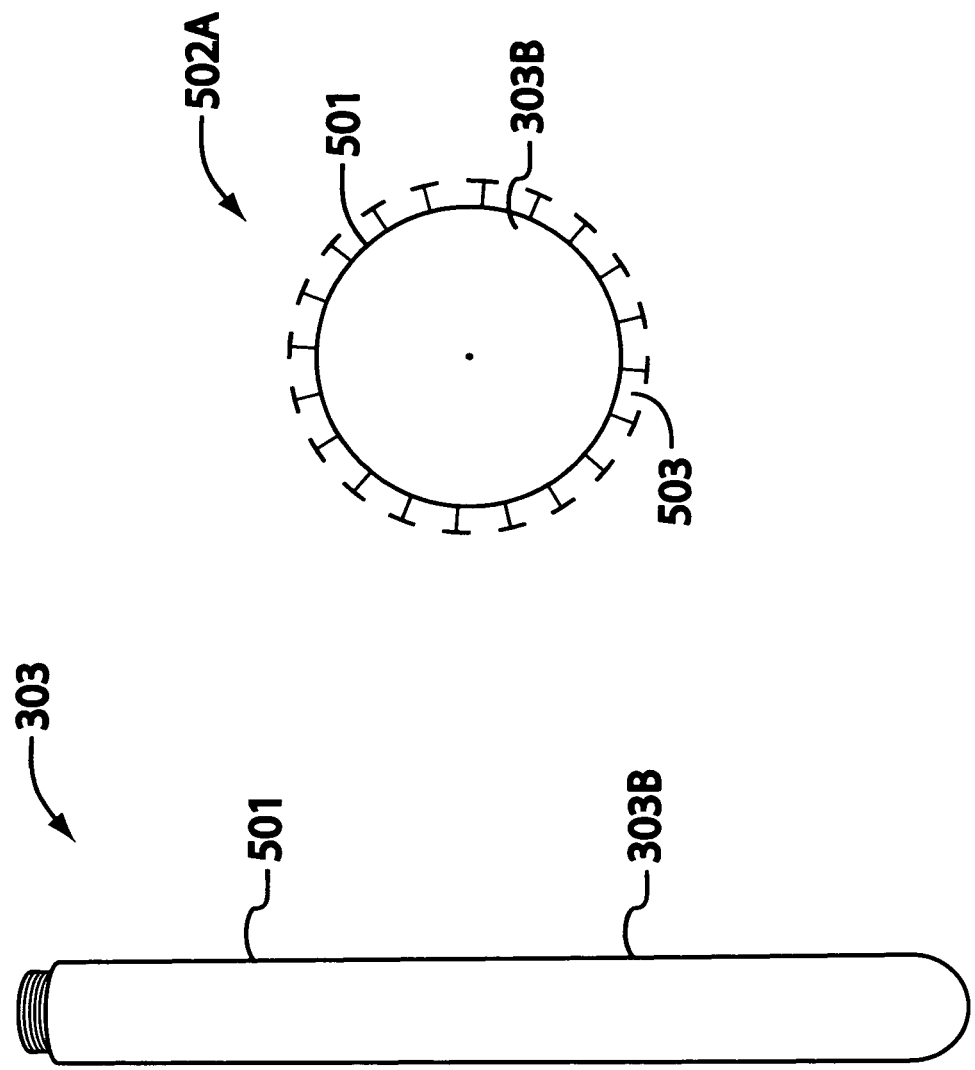
FIG. 5A illustrates stem loading when stem is not texturized.

As illustrated in FIGS. 5A,B, and C, the surface 501 of the stem may be texturized or otherwise treated to increase the surface area of the stem and thereby to increase the carrying capacity of the surface to hold a layer of antibiotic compound, formulated, for example as a paste, on the surface of the stem.

The surface 501 of the stem may be loaded (coated) with the medication compound by painting or otherwise covering the surface. The compound is relatively viscous and physically stable at temperatures near 98.6 F (37.0 C). When the stem is implanted and cemented into place in the femur, the medication slowly liquifies and diffuses around the stem and adjacent, infection sites in the femur tissue. The medication in the smooth surface disperses first, followed by that in surface wells and texturing (micro grooves). The medication moves outward from the stem (to areas of low concentration) and generally downward.

FIGS. 5A,B, and C, respectively, illustrate, but do not limit patterns or types of texturing of the surface 501 the stem leg 303B and the effects such texturing may have on the loading of medication on the stem for treatment of infections of the bone at or near the site of the stem implant.

FIG. 5A is a stem with no texturing. The cross section of the stem 502A shows a comparatively thin layer 503 of medication covering the surface 501 of the stem leg 303B.

Figure 5B:
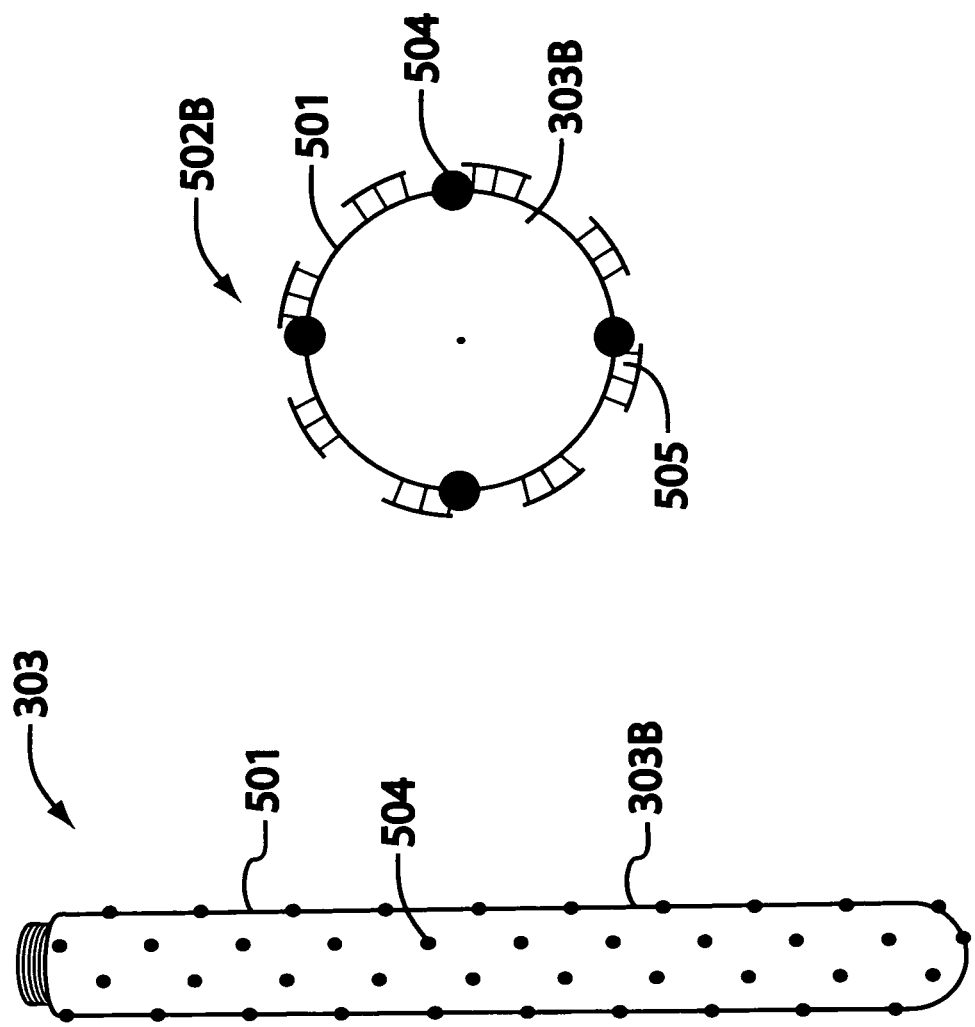
FIG. 5B illustrates stem loading when stem surface is texturized with micro-hemispheres.

FIG. 5B illustrates a stem leg 303B texturized on the surface 501 with a series of micro-bumps (or micro-hemispheres). The texturing increases the surface area of the surface 501 thereby increasing the loading capacity or potential amount of material that will be retained on the stem leg 303B subsequently be released along the stem leg 303B. The cross section 502B shows the micro-hemispheres 504 on the surface 501 and a layer covering the surface, resulting in a layer 505 of medication that is thicker (greater loading) than the comparable layer 503 shown in the cross section 502A with no texturing.

Figure 5C:
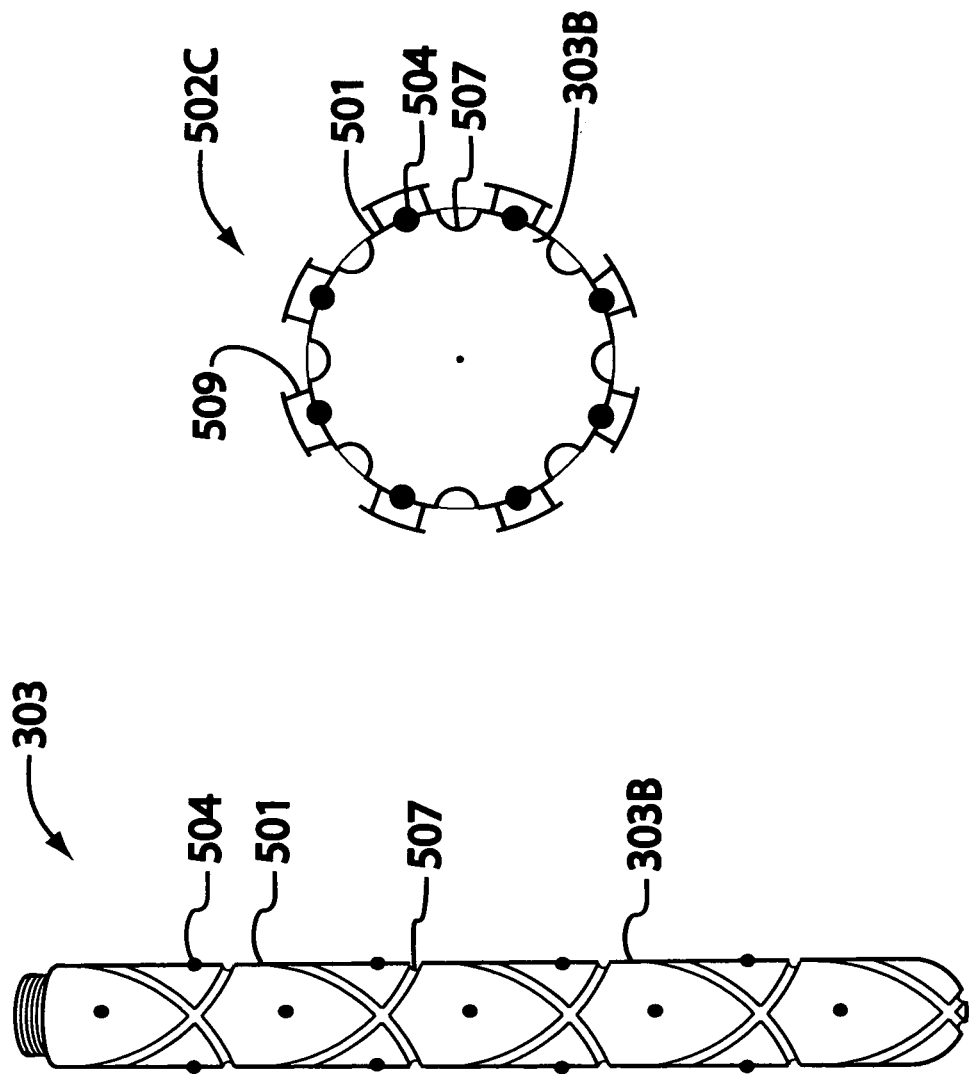
FIG. 5C illustrates stem loading when stem surface is texturized with spiraling microgrooves and micro-spheres.

FIG. 5C is the same stem as shown in FIG. 5B, with the additional texturing in the form of a series of micro-grooves 507 in the surface 501 of the stem leg 303B in addition to micro-hemispheres. The grooves spiral downward along the length of the stem leg. The grooves increase the surface area of the stem leg, thereby increasing the loading capacity of the stem leg 303B, as indicated in cross section 502C by the thickness of the layer 509 of medication compared corresponding layers in FIG. 5A and FIG. 5B, 503 and 505, respectively. Difference shown among the three cross sections 502A, 502B, and 502C are for illustrative purposes and do not represent quantitative differences, as one skilled in the art understands. A variety of additional factors may affect the relative loading potential.

Medication Delivery System

Figures 5D, 5E, 5F:
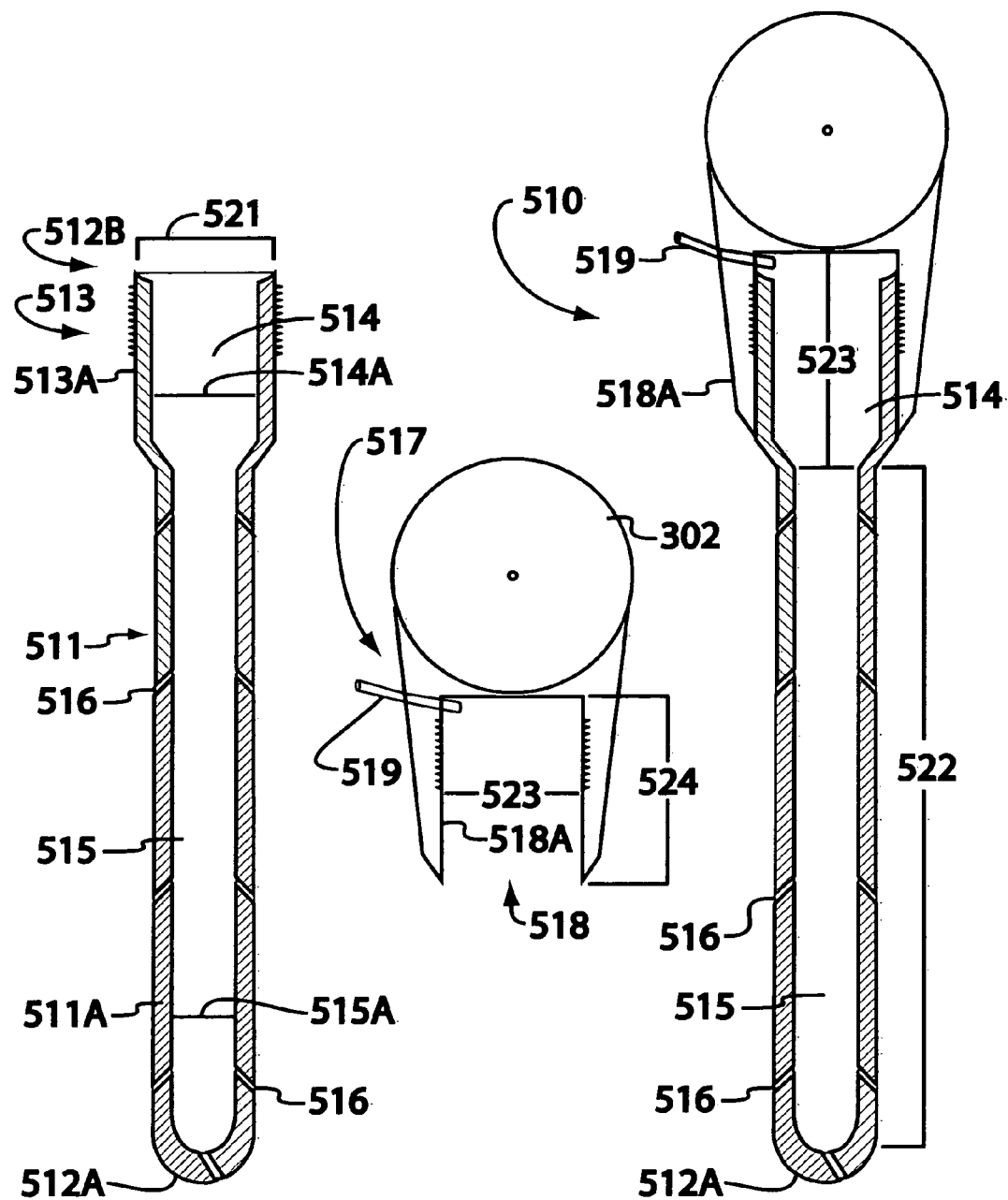
FIG. 5D illustrates modified stem leg as part of medication delivery system.
FIG. 5E illustrates modified stem base as part of medication delivery system.
FIG. 5F illustrates assemble stem modified as part of medication delivery system.

FIGS. 5D,E, and F illustrate modifications to the stem 303 and stem base 303A that comprise a system to facilitates deliver of medication to the stem implant site continuously, following surgery.

As shown in FIGS. 5D and 5E, the modified stem 510 a comprises modified stem leg 513 with a proximal end 512A and a distal end 512B. The distal end comprise an enlarged, threaded post 513A the outside diameter 523A of which is functionally equal to the diameter 523 of the modified base receptacle 518. The enlarged threaded post 513A is bored to form a medication supply reservoir 514. In addition to the modified threaded post, the modified stem leg 511 is bored to form a medication distribution chamber 515. The diameter 515A of the medication distribution chamber 515, by way of illustration, not limitation, is generally at least twice the twice the diameter of the medication distribution chamber 515. A plurality of discharge ports 516 traverses the wall 511A of the stem leg 511.

The modified stem base 517 comprises an enlarge, threaded receptacle 518 that is adapted to engage and secure the enlarge, threaded post 518 in position with respect to the frame 302. The medication supply input tube 519 traverses the enlarged, threaded post wall 513A and the threaded receptacle wall 518A and delivers medication to the medication distribution chamber 515 and the supply reservoir 518. Commonly, medication is delivered to the medication supply input tube 519 under minimal positive pressure by a syringe or comparable instrument (not illustrated) that is in functional communication with an external supply of medication. When the medication distribution chamber 515 and medication supply reservoir 518 are filled, the medication seeps from the plurality of discharge ports 516 and continuously irrigates the interface of the stem leg and cementing material in the femur and disperses in this material through seams and/or any cracks or openings in the material and by other, diffusive forces.

Dispersement of the medication may be enhanced or accelerated by increasing pressure though the input tube by means of a large syringe or comparable device. Increasing pressure slightly is anticipated as part of the process of refilling the medication distribution cavity 515 and medication supply reservoir 518.

Addition Modular Neck/Ball Placement Element

Figure 1A:
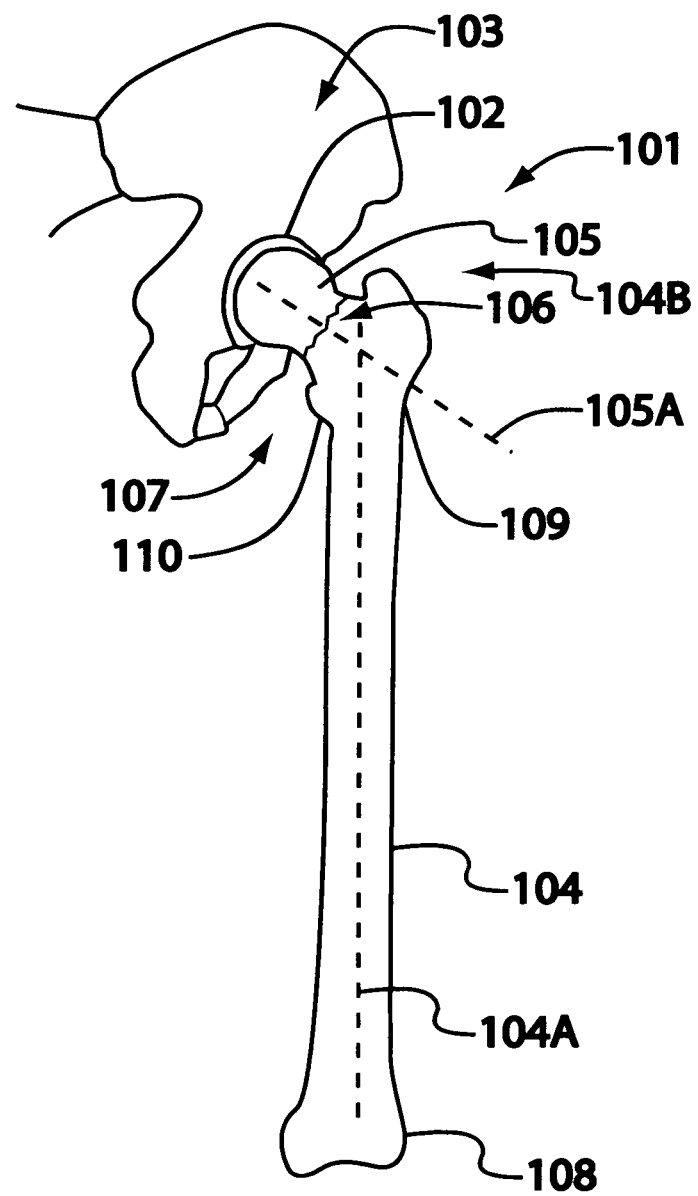
FIG. 1A illustrates a hip joint and femur.

No single aspect of either hip or shoulder replacement surgery or of the prosthetic devices implanted can be designated as the most important or critical aspect of the procedure. Certainly positioning the stem of the prosthetic device in the long bone (femur or humerus, FIGS. 1A and 1B and FIG. 2C) must be viewed as critical. The stem 303 or stem leg 303B anchors the prosthetic device in the long bone, and secure anchoring and optimum alignment of the device with the receptacle (cup) element of the hip or shoulder joint are prerequisite to a successful surgical outcome.

Figure 1B:
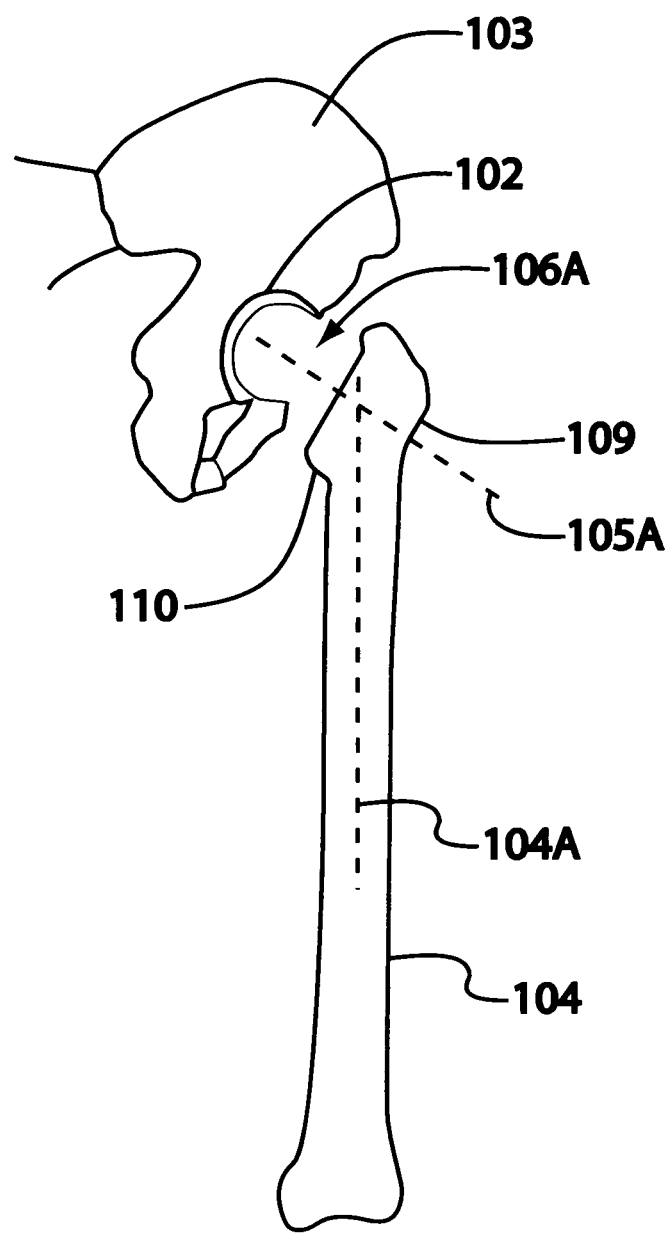
FIG. 1B illustrates the hip joint with part of the neck and ball amputated.
Figure 2A:
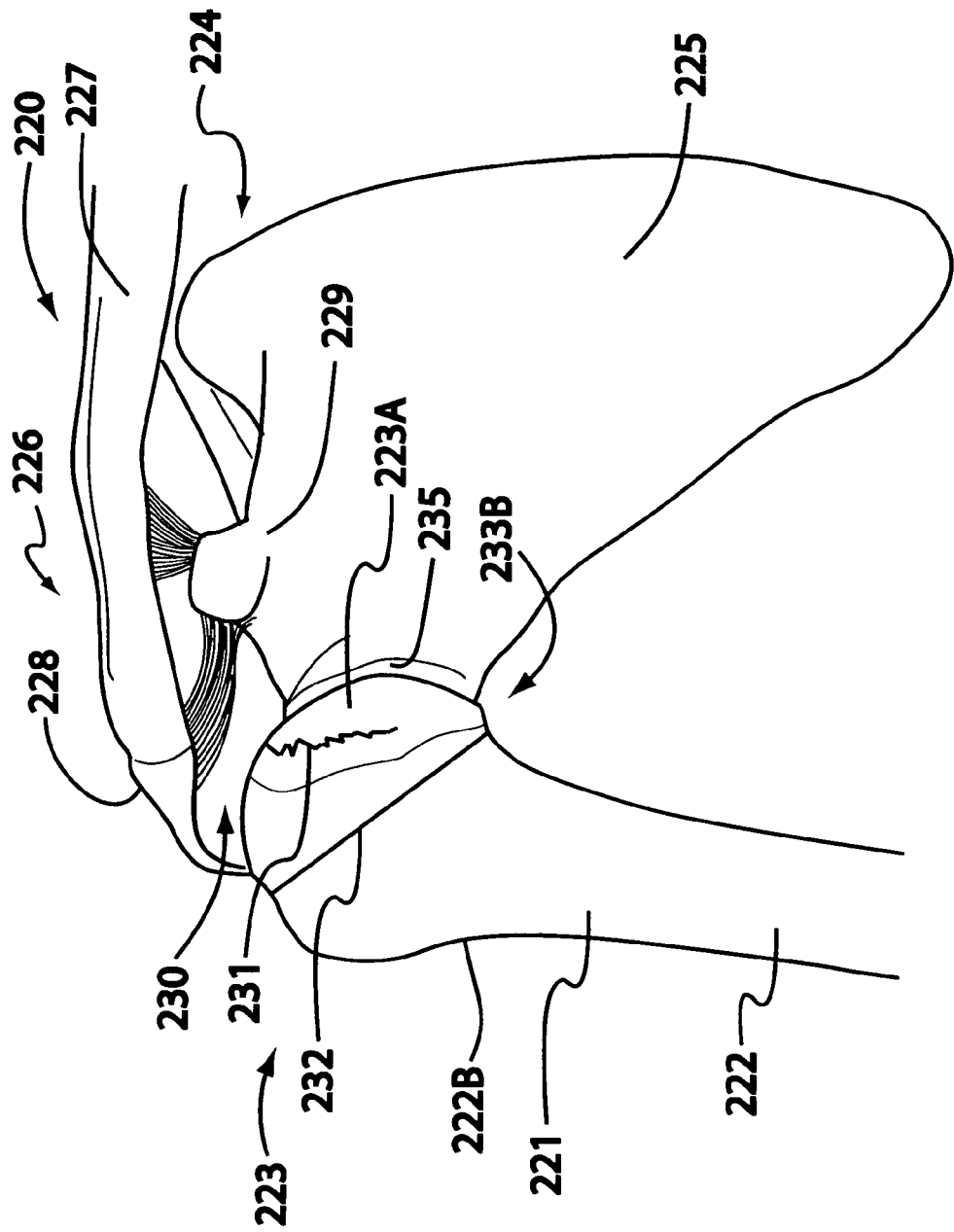
FIG. 2A illustrates a shoulder joint with a fracture in the ball/neck area.
Figure 2B:
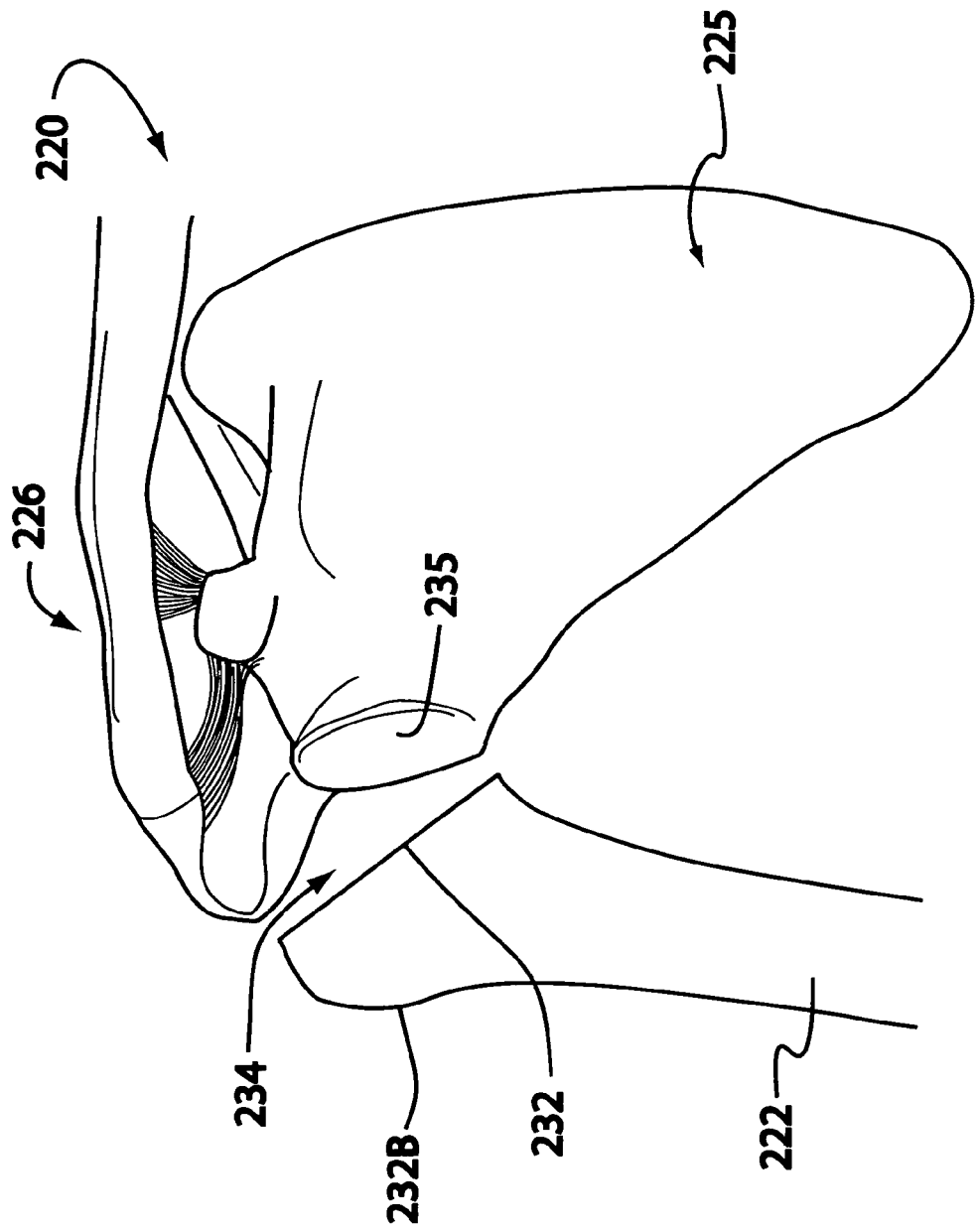
FIG. 2B illustrates the shoulder joint of FIG. 2A with the injured segment amputated.
Figure 2C:
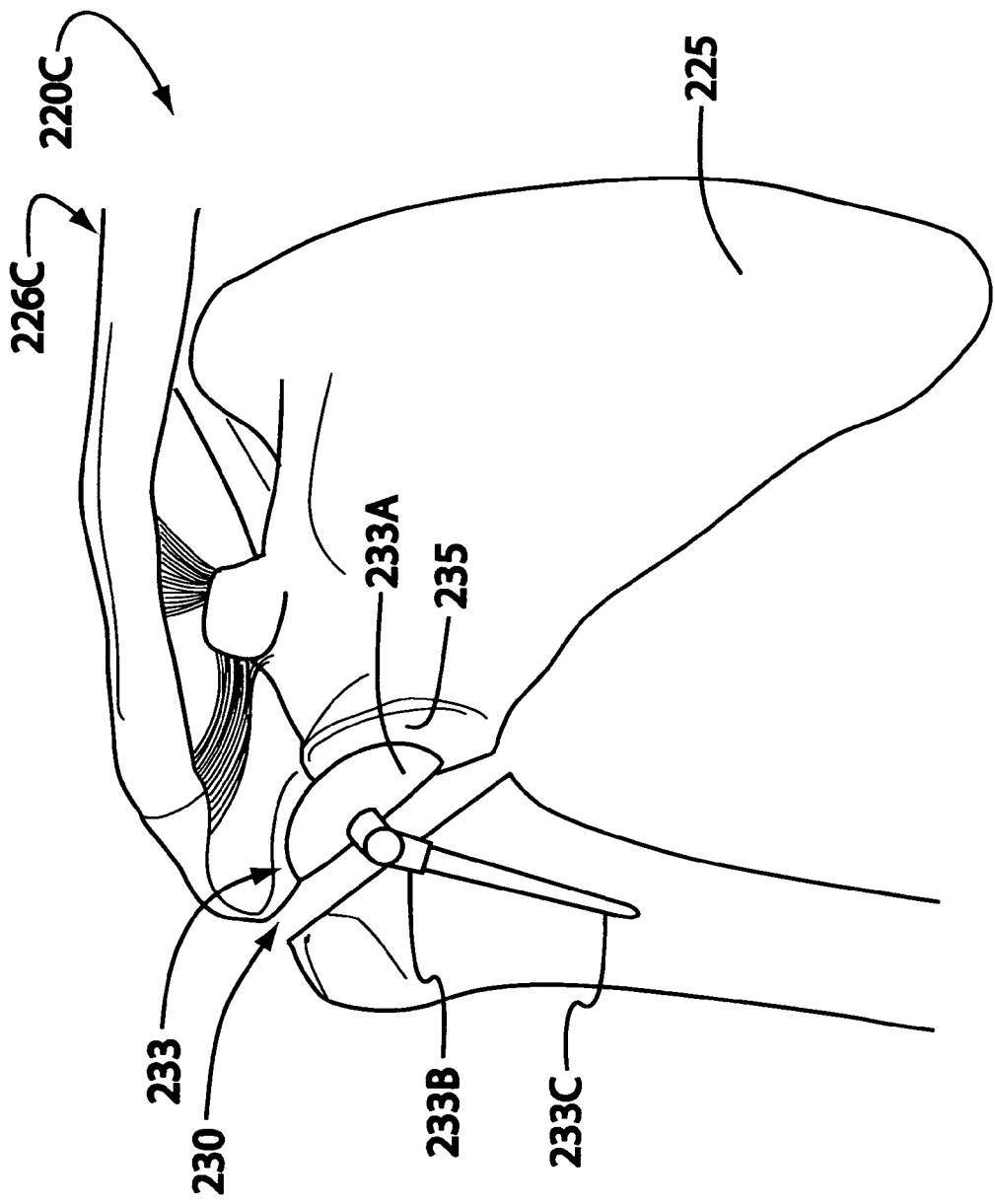
FIG. 2C illustrates the shoulder joint of FIG. 2B with an endoprosthetic joint implanted in the humerus.

Both hip and shoulder replacement surgeries have generally recognized protocols which include minimizing the degree/extent of bone amputated and establishing an optimal plane at the amputation site for positioning and securing the prosthetic device in the long bone and alignment of the joint. An example of a preferred amputations for hip and for shoulder surgery are indicated in FIGS. 1B (hip) and 3A (shoulder). One skilled in the art recognizes that the amputations illustrated in FIGS. 1B and 2A are examples of desirable, minimal amputations, and do not reflect the best approach for any surgery as circumstances may dictate. The greater the required degree amputation, the more complex optimum positioning and securing the prosthetic becomes and the longer the anticipated recovery period becomes.

Figure 6A:
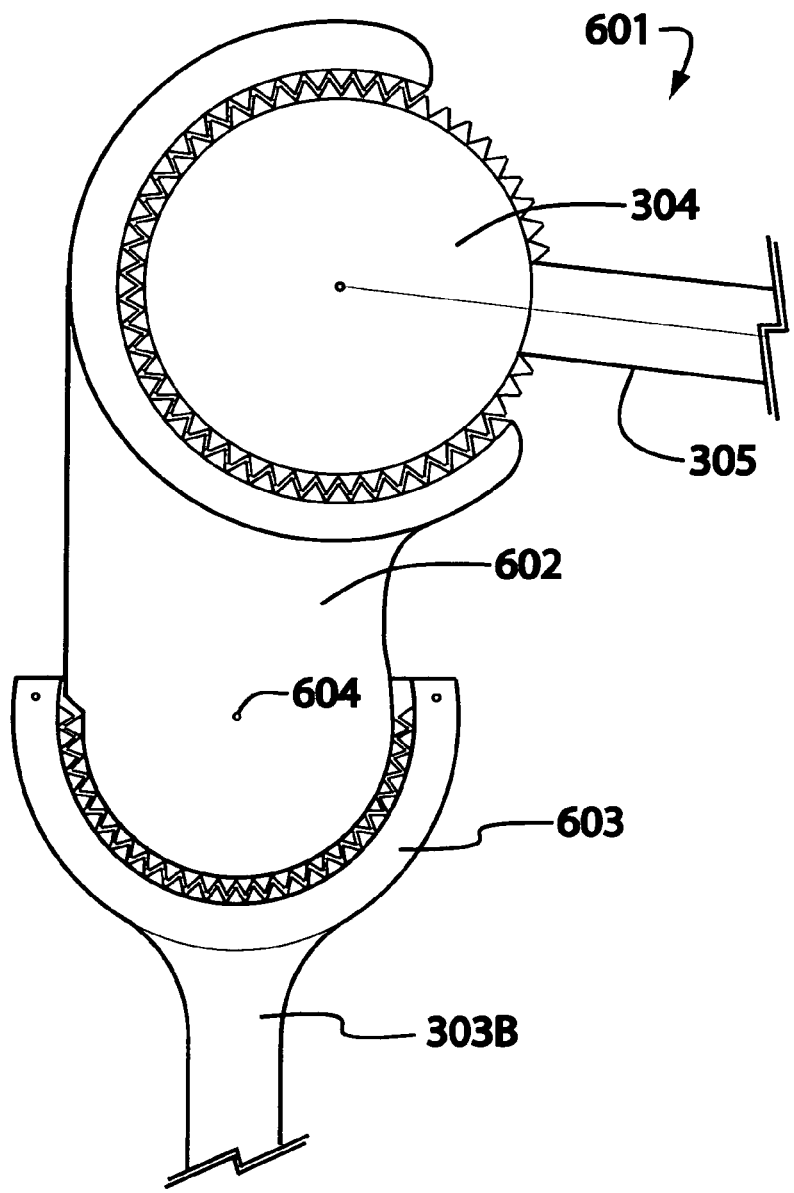
FIG. 6A illustrates of modifications of the base of the frame and top of the stem into a modular unit comprising modular segments that are adjustably connected.
Figure 6B:
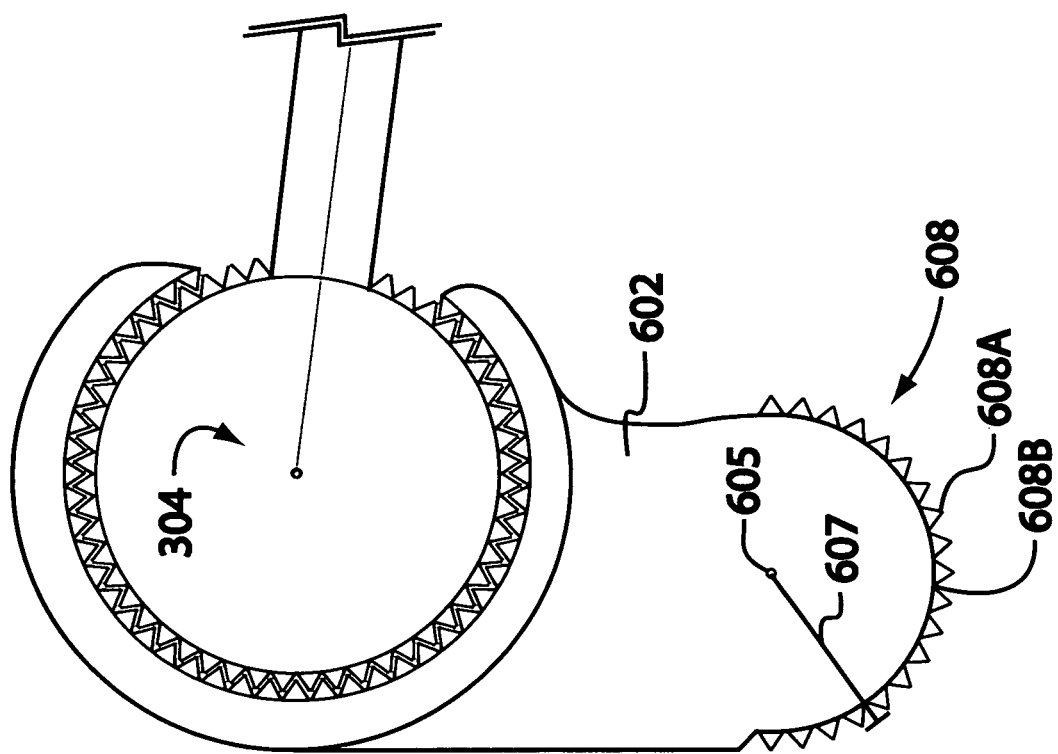
FIG. 6B provides details of the first modular segment.
Figure 6C:
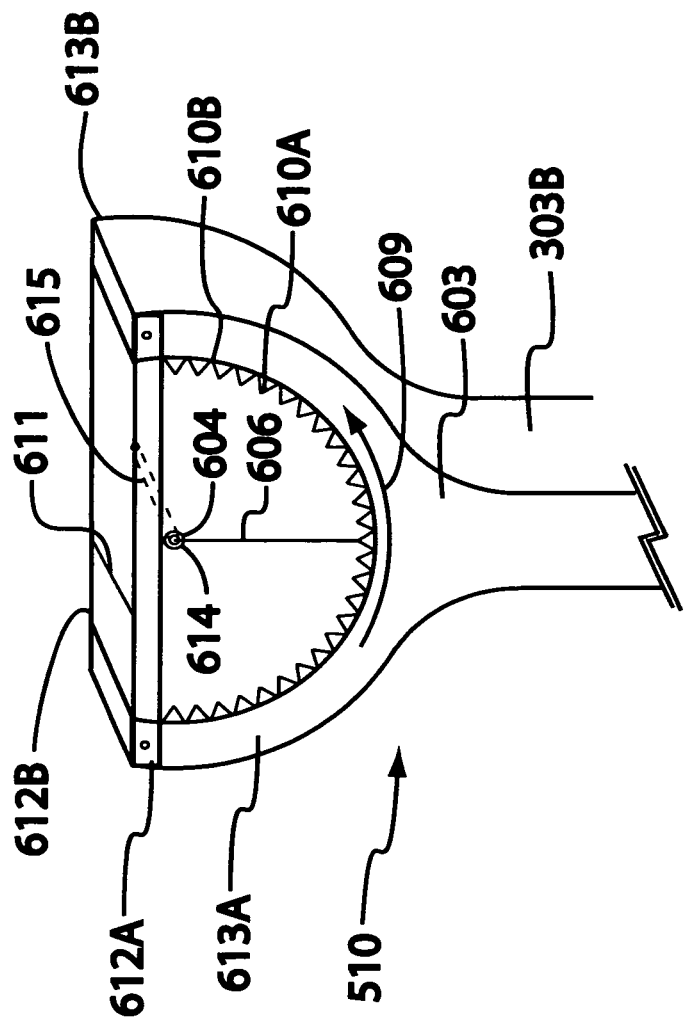
FIG. 6C provides details of the second modular segment.

The modular element 601 of a hip or shoulder prosthetic device illustrated in FIG. 6A provides significant flexibility in adjusting/positioning the stem leg 303B in the long bone (femur or humerus) and in orienting and aligning the neck 305 and ball 306 with the socket element of the joint. In addition, removable, components the modular element 601 simplify removing, adjusting, and repositioning the first modular element 602 and adjusting/positioning the neck 305 and ball 306 in the cup element of the joint. In addition, the modular element 601 comprises two segments, the first modular segment 602 (FIG. 6A and FIG. 6B) and the second modular segment 603 (FIG. 6A and FIG. 6C. The first modular segment 602 comprises a modification of the bottom surface 308A (FIG. 3C) and/or the stem base 303A (FIG. 3C). The perimeter 608 of the first modular segment 602 is described by an arc with a center point 605 and a radius 607. The perimeter 608 of the first modular segment 602 is divided into teeth 608A and complimentary shaped gaps 608B.

The second modular segment 603 (FIG. 6A and FIG. 6C) comprises a modification of the proximal end 510 of the stem leg 303B. The perimeter arrow 609 of the second modular element 603 is described by an arc with center point 604 and radius 606. The perimeter of the second modular segment arrow 609 is divided into teeth 610A and intervening, complimentary gaps 610B. The radius 606 of the second modular segment 603 equals the radius 604 of the first modular segment.

The second modular segment has a width 611 which width 611 equals the same dimension (not indicated) of the first modular segment 602

The modular unit 601 may be assembled before or during surgery. The stem leg 303B is inserted into the long bone (femur or humerus). The first modular segment 602 slides into and engages the complimentary teeth/gaps in the opposing perimeter 609 of the second modular segment 603. The first modular segment may be inserted, removed, and reinserted to adjust the position of the second modular segment 603 with respect to the first modular segment 602 and with respect to positioning and orientation of the neck 305 and ball 306, as well as to reposition the stem leg 303B as may be required based on conditions of the face of the amputated long bone and related considerations understood by those skilled in the art.

Locking bars 612A and 612B are connected to the first 613A and second 613B face, respectively, of the second modular segment 603. A support axle chases traverses the locking bars and the first modular segment on a line extending from center point 604. A support axle 615 extends through the support axle chase 614 and is anchored at a center point in each locking bar 612A/B, thereby securing the first modular segment 602 to the second modular segment 603 by maintaining the engagement of the complimentary teeth and gaps 608A/B engaged with 610A/B respectively. The locking bars 612A and 612B prevent lateral movement that might separate or modify the established, optimal relationship of the two modular segments.

As one skilled in the art appreciates, the modular configuration of the prosthesis provides flexibility to remove and reorient/reposition various segments or components of the prosthesis during surgery to address unanticipated conditions. The two modular segments 602 and 603 are separated by removing the locking axle 615, removing at least one of the locking bars 612A/612B and separating the first and second modular segments. The stem leg can be removed and repositioned by adjusting the relationship between the first and second modular segments, and the neck positioning cylinder can be unlocked and rotated to reposition the ball 306 in the joint cup.

I claim:

1. A modular, adjustable, prosthetic hip and shoulder spacer comprising a frame and a neck positioning cylinder and wherein the longitudinal axis of said neck positioning cylinder is in a horizontal plane in relation to the vertical plane of the centerline of said frame; and wherein said frame is manufactured from a single piece of metallic material; wherein said frame comprises a neck positioning cradle unit wherein said neck positioning cradle unit comprises a semicircular cradle bed; and further wherein said neck positioning cylinder comprises a cylinder with a first end and a second end, and a circumference face; and further wherein said neck positioning cylinder comprises an axle chase and an axle wherein said axle chase traverses the full length of the longitudinal centerline of said neck positioning cylinder and further, wherein said axle extends through the full length of said axle chase, and further, wherein said neck positioning cylinder rotates around said axle, in a vertical plane, and further wherein said frame comprises a second upper face and a second lower face, wherein said axle mechanically secures said neck positioning cylinder to said second upper face of said frame wherein said modular, adjustable, prosthetic hip and shoulder spacer comprises a stem base, wherein, said stem base is structurally contiguous with said frame, and further wherein said stem base comprises a threaded, female receptacle and further, wherein said modular, adjustable, prosthetic hip and shoulder spacer comprises a leg stem wherein said leg stem comprises a proximal end and a distal end, wherein the proximal end of said leg stem is threaded functionally to engage said threaded female receptacle, and the distal end of said leg stem is adapted to engage and secure said stem leg to the fibula; and further, wherein said neck positioning cylinder is longitudinally traversed by the members of a set of locking pin chases and wherein said second upper face of said frame is traversed by members of a set of complimentary threaded, locking pin anchor receptacles; and further wherein said members of said set of locking pin chases and the members of said set of locking pin anchor receptacles are located on and respectively positioned according to a first arc and a second arc, wherein said first arc and said second arc have a common length radius, and wherein the center point of said axle is extended as the center point of said first arc and said second arc; and wherein said first arc defines the positioning of the members of said set of locking pin chases on said first end of said neck positioning cylinder, and the positioning of the members of said set of locking pin anchor receptacles is defined by said second arc on said upper second half of said frame; and further, wherein said members of said set of locking pin chases and said members of said locking pin anchor receptacles are positioned and spaced so that only a specific member of said set of locking pin chases is aligned with a specific, complimentary member of said set of locking pin anchor receptacles; and whereas, the spacing between the members of said set locking pin chases is equally spaced on said first arc.

2. A modular, adjustable, prosthetic hip and shoulder spacer comprising a frame and a neck positioning cylinder and wherein the longitudinal axis of said neck positioning cylinder is in a horizontal plane in relation to the vertical plane of the centerline of said frame; and wherein said frame is manufactured from a single piece of metallic material; wherein said frame comprises a neck positioning cradle unit, wherein said neck positioning cradle unit comprises a semicircular cradle bed and further wherein said neck positioning cylinder comprises a cylinder with a first end and a second end and a circumference face; and further, wherein said neck positioning cylinder comprises an axle chase and an axle, wherein said axle chase traverses the full length of the longitudinal centerline of said neck positioning cylinder, and further, wherein, said axle extends through the full length of said axle chase, and further, wherein said neck positioning cylinder rotates around said axle, in a vertical plane, and further wherein said frame comprises a second, upper face and a second lower face, wherein said axle mechanically secures said neck positioning cylinder to said second upper face of said frame, and further, wherein the cylinder circumference face and the bed floor of said semi-circular bed cradle of said frame of said modular, adjustable prosthetic hip and shoulder spacer are shaped into complimentary sets of opposing, parallel groves and ridges; thus, when said neck positioning cylinder is positioned in said semi-circular cradle bed, said opposing grooves and ridges engage and functionally prevent said neck positioning cylinder from rotating around said axle; and further, wherein said axle traverses the core of said neck positioning cylinder and engages a receptacle positioned on said second upper face of said frame, thereby connecting said neck positioning cylinder to said frame.

3. The modular, adjustable, prosthetic, hip and shoulder spacer of claim 1 wherein the bottom of said frame and the stem base and the proximal end of the stem leg are modified to form a positioning unit; said positioning unit comprises a first, male segment and a second, female segment; wherein, the perimeter of said first, male segment, formed from the bottom of said frame and from said stem base, comprises a first arc with a first center point and a first radius, and further wherein the perimeter of said first, male segment comprises a first series of teeth and complementing spaces between each pair of teeth; and, wherein, the perimeter of said second, female segment, formed from said proximal end of said stem leg, comprises a second arc with a second center point and a second radius; and further, wherein said perimeter of said second, female segment comprises a second series of teeth with complementing spaces between each pair of teeth; and, wherein said first and said second center points are the same point and said first radius and said second radius are equal; and further, wherein, said perimeter of said first, male segment is positioned such that said first series of teeth and complementing spaces engage the opposing second series of teeth and complementary spaces such that the angle of a center line of the stem can be adjusted in relation to a center line of the frame and of the neck and ball as the stem leg is implanted in the long bone; the second, female segment further comprises a first and a second face and a pair of locking bars wherein each member of the pair of locking bars comprises a support axle chase and further wherein one member of said pair of locking bars is mechanically attached at each end to said first face and the second member of said pair of locking bars is attached to each end of said second face; and further wherein a support axle traverses said first locking bar, said first, male segment, and said locking bar and secures said first, male segment and secure said second, female segment engaging said first series of teeth and spaces with said second, opposing, series of teeth and spaces.

4. A modular, adjustable, prosthetic hip and shoulder spacer comprising a frame and a neck positioning cylinder; and wherein the longitudinal axis of said neck positioning cylinder is in a horizontal plane in relation to the vertical plane of the centerline of said frame; and wherein said frame is manufactured from a single piece of metallic material; wherein said frame comprises a neck positioning cradle unit wherein said neck positioning cradle unit comprises a semi-circular cradle bed and further wherein said neck positioning cylinder comprises a cylinder with a first end and a second end, and a circumference face; and further, wherein said neck positioning cylinder comprises an axle chase and an axle wherein said axle chase traverses the full length of the longitudinal centerline of said neck positioning cylinder and further said axle extends through the full length of said axle chase and further said neck positioning cylinder rotates around said axle in a vertical plane and further wherein said frame comprises a second upper face and a second lower face wherein said axle mechanically secures said neck positioning cylinder to said second upper face of said frame; and further, wherein modular, adjustable, prosthetic hip and shoulder spacer further comprise a system to facilitate delivery of medication to a stem implant site; wherein said system to facilitate delivery of medication to the stem implant site comprises a stem, wherein said stem comprises a stem leg, wherein said stem leg comprises a distal and a proximal end and wherein said proximal end comprises a threaded post, wherein said threaded post has a distal end and a proximal end and wherein said distal end of said threaded post comprises a medication supply reservoir; wherein the internal diameter of said medication supply reservoir is greater than the internal diameter of said stem and wherein said stem is contiguous with said threaded post; and further wherein said frame of said modular, adjustable, prosthetic hip and shoulder spacer comprises a base receptacle wherein the outside diameter of said proximal end of said threaded post is effectively equal in diameter to the diameter of said base receptacle and finally wherein said system to facilitate delivery of medication to to the implant site further comprises a medication input tube wherein said medication input tube is under pressure produced by external means wherein said external means are in fluid communication with said medication supply reservoir, and further, wherein said medication is transferred from said medication distribution chamber to said surgical site through a plurality of distribution ports, wherein said distribution ports traverse the walls of said medication discharge chamber, and, wherein, said system to facilitate delivery of medication to the implant site further comprises a medication input tube that is under pressure produced by external means, wherein said external means are in fluid communication with said medication supply reservoir, and further, wherein said medication is transferred from said medication distribution chamber to said surgical site through a plurality of distribution ports, wherein said distribution ports traverse the wall of said medication discharge chamber.

* * * * *